(12) United States Patent
Viola et al.

(10) Patent No.: US 10,098,638 B2
(45) Date of Patent: Oct. 16, 2018

(54) BATTERY POWERED SURGICAL INSTRUMENT

(71) Applicant: Covidien LP, Mansfield, MA (US)

(72) Inventors: Frank J. Viola, Sandy Hook, CT (US); Gregg Krehel, Newtown, CT (US); Guido Pedros, Shelton, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 15/450,661

(22) Filed: Mar. 6, 2017

(65) Prior Publication Data

US 2017/0172573 A1    Jun. 22, 2017

Related U.S. Application Data

(63) Continuation of application No. 13/955,374, filed on Jul. 31, 2013, now Pat. No. 9,585,659, which is a
(Continued)

(51) Int. Cl.
*A61B 17/072* (2006.01)
*A61B 17/00* (2006.01)
(Continued)

(52) U.S. Cl.
CPC .. *A61B 17/07207* (2013.01); *A61B 17/00234* (2013.01); *A61B 17/068* (2013.01);
(Continued)

(58) Field of Classification Search
CPC . A61B 17/068; A61B 17/0686; A61B 17/072; A61B 17/07207; A61B 17/115;
(Continued)

(56) References Cited

U.S. PATENT DOCUMENTS 37,165 A    12/1862   Gary
3,079,606 A   3/1963   Bobrov et al.
(Continued)

FOREIGN PATENT DOCUMENTS

CA    2155476 A1    4/1996
EP    0647431 A2    4/1995
(Continued)

OTHER PUBLICATIONS

Detemple, P., "Microtechnology in Modem Health Care", Med Device Technol., 9(9):18-25 (1998).
(Continued)

*Primary Examiner* — Scott A. Smith

(57) ABSTRACT

A powered endoscopic surgical apparatus is provided and includes a handle including a housing, a power source supported in the housing; an endoscopic portion extending distally from the housing of the handle; an end effector assembly coupled to a distal end of the endoscopic portion, the end effector assembly including a pair of jaws configured to perform a surgical function; a driving member; a drive source including a motor powered by the power source and connected to the driving member; and a gear assembly engaged with the motor. The gear assembly including a gear rack provided on the driving member; and a main gear operatively connected with the gear rack, the motor spinning the main gear such that rotary motion of the main gear moves the driving member in an axial direction such that the driving member actuates the end effector to perform the surgical function.

15 Claims, 25 Drawing Sheets

Related U.S. Application Data continuation of application No. 13/442,141, filed on Apr. 9, 2012, now Pat. No. 8,505,799, which is a continuation of application No. 13/052,871, filed on Mar. 21, 2011, now Pat. No. 8,348,125, which is a continuation of application No. 12/247,733, filed on Oct. 8, 2008, now Pat. No. 7,909,221, which is a continuation of application No. 11/446,283, filed on Jun. 2, 2006, now Pat. No. 7,461,767.

(60) Provisional application No. 60/687,406, filed on Jun. 3, 2005, provisional application No. 60/687,244, filed on Jun. 3, 2005.

(51) Int. Cl.
*A61B 17/068* (2006.01)
*A61B 17/29* (2006.01)

(52) U.S. Cl.
CPC .. *A61B 17/072* (2013.01); *A61B 2017/00022* (2013.01); *A61B 2017/00128* (2013.01); *A61B 2017/00132* (2013.01); *A61B 2017/00398* (2013.01); *A61B 2017/00734* (2013.01); *A61B 2017/07214* (2013.01); *A61B 2017/07257* (2013.01); *A61B 2017/07271* (2013.01); *A61B 2017/07285* (2013.01); *A61B 2017/2943* (2013.01)

(58) Field of Classification Search
CPC ...... A61B 17/1155; A61B 2017/07214; A61B 2017/00398; A61B 2017/00734; A61B 2017/2943
USPC .............. 227/19, 175.1, 175.2, 176.1, 180.1; 606/139, 153, 219
See application file for complete search history.

(56) References Cited

U.S. PATENT DOCUMENTS

| | | |
|---|---|---|
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,091,880 A | 5/1978 | Troutner et al. |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Yates |

(56) References Cited

U.S. PATENT DOCUMENTS

| | | |
|---|---|---|
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H001904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H002037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |

(56) References Cited

U.S. PATENT DOCUMENTS

| | | |
|---|---|---|
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,348,125 B2 | 1/2013 | Viola et al. |
| 8,419,768 B2 | 4/2013 | Marczyk |
| 8,459,522 B2 | 6/2013 | Marczyk |
| 8,479,967 B2 | 7/2013 | Marczyk |
| 8,505,799 B2 | 8/2013 | Viola et al. |
| 8,506,557 B2 | 8/2013 | Zemlok et al. |
| 8,636,766 B2 | 1/2014 | Milliman et al. |
| 8,939,343 B2 | 1/2015 | Milliman et al. |
| 9,289,211 B2 | 3/2016 | Williams et al. |
| 9,370,361 B2 * | 6/2016 | Viola ............... A61B 17/07207 |
| 9,532,782 B2 * | 1/2017 | Kostrzewski .... A61B 17/07207 |
| 9,585,659 B2 | 3/2017 | Viola et al. |
| 2002/0025891 A1 | 2/2002 | Colosky et al. |
| 2002/0103489 A1 | 8/2002 | Ku |
| 2002/0111641 A1 | 8/2002 | Peterson et al. |
| 2002/0165541 A1 | 11/2002 | Whitman |

(56) References Cited

U.S. PATENT DOCUMENTS

| | | |
|---|---|---|
| 2003/0073981 A1 | 4/2003 | Whitman et al. |
| 2003/0090201 A1 | 5/2003 | Peng |
| 2003/0114851 A1 | 6/2003 | Truckai et al. |
| 2003/0120306 A1 | 6/2003 | Burbank et al. |
| 2003/0139746 A1 | 7/2003 | Groiso |
| 2003/0225411 A1 | 12/2003 | Miller |
| 2004/0094597 A1 | 5/2004 | Whitman et al. |
| 2004/0232199 A1 | 11/2004 | Shelton et al. |
| 2004/0232200 A1 | 11/2004 | Shelton et al. |
| 2004/0232201 A1 | 11/2004 | Wenchell et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006434 A1 | 1/2005 | Wales et al. |
| 2005/0010235 A1 | 1/2005 | VanDusseldorp |
| 2005/0023324 A1 | 2/2005 | Doll et al. |
| 2005/0067458 A1 | 3/2005 | Swayze et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0187576 A1 | 8/2005 | Whitman et al. |
| 2005/0192609 A1 | 9/2005 | Whitman et al. |
| 2005/0228341 A1 | 10/2005 | Edgerley |
| 2005/0247753 A1 | 11/2005 | Kelly et al. |
| 2006/0000867 A1 | 1/2006 | Shelton et al. |
| 2006/0022014 A1 | 2/2006 | Shelton et al. |
| 2006/0022015 A1 | 2/2006 | Shelton et al. |
| 2006/0097025 A1 | 5/2006 | Milliman et al. |
| 2006/0151567 A1 | 7/2006 | Roy |
| 2006/0175375 A1 | 8/2006 | Shelton et al. |
| 2006/0278659 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0084896 A1 | 4/2007 | Doll et al. |
| 2007/0084897 A1 | 4/2007 | Shelton et al. |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0125826 A1 | 6/2007 | Shelton |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1 | 8/2007 | Shelton et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2009/0138006 A1 | 5/2009 | Bales et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0220989 A1 | 8/2012 | Zemlok et al. |
| 2012/0223121 A1 | 9/2012 | Viola et al. |

FOREIGN PATENT DOCUMENTS

| | | |
|---|---|---|
| EP | 0738501 A1 | 10/1996 |
| EP | 0770354 A1 | 5/1997 |
| EP | 537570 B1 | 1/1998 |
| EP | 1070487 A2 | 1/2001 |
| EP | 1 201 196 A1 | 5/2002 |
| EP | 1 658 817 A1 | 5/2006 |
| EP | 1813203 A2 | 8/2007 |
| FR | 2 849 589 A1 | 7/2004 |
| WO | 94/14129 A1 | 6/1994 |
| WO | 9729694 A1 | 8/1997 |
| WO | 9740760 A1 | 11/1997 |
| WO | 9837825 A1 | 9/1998 |
| WO | 9952489 | 10/1999 |
| WO | 2002/34140 A2 | 5/2002 |
| WO | 2003/026511 A1 | 4/2003 |
| WO | 2003/030743 A2 | 4/2003 |
| WO | 2004002760 A2 | 4/2004 |
| WO | 2007030753 A2 | 3/2007 |
| WO | 2007118179 A2 | 10/2007 |
| WO | 2007014355 A3 | 4/2009 |

OTHER PUBLICATIONS

European Search Report corresponding to EP 06 02 6840, dated Apr. 17, 2007.
International Search Report for corresponding PCT Application PCT/US06/21524, dated May 28, 2008.
European Search Report corresponding to EP 08 25 3184.9, dated Feb. 27, 2009.
European Search Report corresponding to EP 08 25 1357.3, dated Sep. 29, 2009.
European Search Report corresponding to EP 08 25 2703.7, dated Oct. 31, 2008.
European Search Report—partial corresponding to EP 10251416 dated Nov. 2, 2010.
European Search Report—extended corresponding to EP 10251416 dated Mar. 3, 2011.
European Search Report corresponding to EP 10252080.6 dated Apr. 18, 2011.

(56) References Cited

OTHER PUBLICATIONS

Canadian Office Action corresponding to counterpart Int'l Appln. No. CA 2,890,787, dated May 2, 2016.

* cited by examiner

BATTERY POWERED SURGICAL INSTRUMENT

CROSS REFERENCE TO RELATED APPLICATIONS

This patent application is a Continuation application claiming the benefit of and priority to U.S. patent application Ser. No. 13/955,374, filed on Jul. 31, 2013 (now U.S. Pat. No. 9,585,659), which is a Continuation application claiming the benefit of and priority to U.S. patent application Ser. No. 13/442,141, filed on Apr. 9, 2012 (now U.S. Pat. No. 8,505,799), which is a Continuation application claiming the benefit of and priority to U.S. patent application Ser. No. 13/052,871, filed on Mar. 21, 2011 (now U.S. Pat. No. 8,348,125), which is a Continuation application claiming the benefit of and priority to U.S. patent application Ser. No. 12/247,733, filed on Oct. 8, 2008 (now U.S. Pat. No. 7,909,221), which is a Continuation application claiming the benefit of and priority to U.S. patent application Ser. No. 11/446,283, filed on Jun. 2, 2006 (now U.S. Pat. No. 7,461,767), which claims the benefit of and priority to U.S. Provisional Patent Application Ser. No. 60/687,406 to Viola, et al., filed on Jun. 3, 2005 which is herein incorporated by reference in its entirety.

U.S. patent application Ser. No. 11/446,283, filed on Jun. 2, 2006 (now U.S. Pat. No. 7,461,767) also claims the benefit of and priority to U.S. Provisional Patent Application Ser. No. 60/687,244 to Viola, et al., filed on Jun. 3, 2005, which is also herein incorporated by reference in its entirety.

U.S. patent application Ser. No. 11/446,283, filed on Jun. 2, 2006 (now U.S. Pat. No. 7,461,767), also relates to U.S. patent application Ser. No. 11/446,282, filed on Jun. 2, 2006 (now U.S. Pat. No. 7,464,847), which is herein incorporated by reference in its entirety.

BACKGROUND

1. Technical Field

The present disclosure relates to surgical instruments. More particularly, the present disclosure relates to a surgical stapling device that has an improved and internally powered driving mechanism.

2. Background of the Related Art

Surgeons have recognized in the art the benefits of a compact surgical apparatus for the application of surgical clips and staples to body tissue in a number of different medical procedures. Often, prior art surgical staplers require some degree of physical force or lateral movement in order to operate a handle to actuate the surgical stapler and fire the staple after a compression to actuate the surgical stapler and fire the staple after a compression of tissue is made. It would be desirable to have a precise surgical stapler device that is compact and easy to use and will quickly and easily fire. Also, once compression of the desired stapling location is made, only a very limited degree of force to the surgical stapling device should be required in order to complete the actuation of the device and thus firing of the staples such as by actuating a trigger switch. Moreover, such a powered stapling device should be very easy to manipulate and hold by the surgeon.

Attempts have been made in the art to provide such a surgical stapling device that is pneumatic or gas powered and/or also externally powered in order to remedy this desire. However, it would be beneficial to provide a disposable apparatus for the application of staples to body tissue that is self contained, self powered and easy to manufacture.

Additionally, tissue exhibits visco-elastic properties. Once under pressure from a jawed structure such as an approximation device of a surgical stapler, the body tissue will slowly compress. Blood and other fluid traverses from the high pressure or gripped area to another low pressure or adjacent area. Once released, as expected the fluid will return from the adjacent area to the previously compressed area.

Prior art surgical stapling devices will approximate tissue. Then, once the approximation is made, the surgeon will introduce the staple into the body tissue.

It is desirable to provide a surgical stapler device that result in a uniform staple formation. It is also desirable to provide a surgical stapler device that allows for an appropriate time interval to elapse for tissue compression. This allows for the blood and fluid to travel away from the compressed area. Compression by an approximation device reduces the amount of blood and fluid therebetween. Without such compression, an uncompressed body tissue remains thicker whereas the compressed body tissue would be thinner, and more compact. The surgeon must control compression time by observing the tissue or by using a separate timing device.

Accordingly, compression of the tissue for the proper amount of time is important for a proper and uniform staple formation due to this viscoelastic tissue phenomenon.

SUMMARY

According to a first aspect of the present disclosure, there is provided a surgical stapler. The stapler has a handle assembly including a stationary handle and a trigger. The trigger is configured to manipulate a cam member through an actuating stroke. The stapler has an elongated body extending distally from the handle assembly and defining a longitudinal axis with a staple cartridge supported adjacent the distal end of the elongated body and containing a plurality of staples. The stapler has an anvil pivotally mounted in relation to the cartridge adjacent the distal end of the elongated body. The anvil has a fastener forming surface thereon and is mounted for pivotal movement in relation to the cartridge between an open position having a distal end spaced from the staple cartridge and a closed position in close cooperative alignment with the staple cartridge. The stapler has an actuation sled supported within the cartridge. The actuation sled is movable to urge the plurality of staples from the cartridge. The stapler also has a drive assembly with a body having a working end and a cam member supported on the working end. The cam member is positioned to translate relative to the anvil to maintain the anvil in the closed position during firing of the stapler.

The trigger is operatively connected to a power cell. The power cell is operably connected to a motor of the drive assembly. The manipulation of the trigger actuates the power cell such that the power cell powers the drive assembly to effect translation of the cam member relative to the anvil. The stapler also has a channel for supporting the staple cartridge and the motor of the drive assembly controls the actuation sled supported within the cartridge. The actuation sled urges the plurality of staples from the cartridge when the anvil is in the closed position and in cooperative alignment with the staple cartridge.

According to another aspect of the present disclosure, there is provided a surgical stapler. The stapler has a handle assembly with a stationary handle and a trigger configured to manipulate a cam member through an actuating stroke. The stapler also has an elongated body extending distally from the handle assembly and defining a longitudinal axis. The stapler also has a staple cartridge supported adjacent the distal end of the elongated body and containing a plurality of staples with an anvil pivotally mounted in relation to the cartridge adjacent the distal end of the elongated body. The anvil has a fastener forming surface thereon and is mounted for pivotal movement in relation to the cartridge between an open position having a distal end spaced from the staple cartridge and a closed position in close cooperative alignment with the staple cartridge.

The stapler has an actuation sled supported within the cartridge. The actuation sled moves to urge the plurality of staples from the cartridge. The actuation sled is connected to a drive rack. The drive assembly has a body with a working end and a cam member supported on the working end. The cam member is positioned to translate relative to the anvil to maintain the anvil in the closed position during firing of the stapler.

The trigger is operatively connected to a power cell. The power cell is operably connected to a motor of the drive assembly such that manipulation of the trigger actuates the power cell such that the power cell powers the drive assembly to effect translation of the cam member relative to the anvil. The stapler also has a channel for supporting the staple cartridge. The motor of the drive assembly controls the actuation sled supported within the cartridge. The actuation sled urges the plurality of staples from the cartridge when the anvil is in the closed position and in cooperative alignment with the staple cartridge.

The stapler also has a protective casing. The protecting casing houses the power cell and the motor in the protective casing and is connected to the stationary handle. The motor has a motor drive shaft that extends through the stationary handle to connect with the drive rack.

According to another aspect of the present disclosure, the surgical stapler is powered by an inexpensive disposable power source that may be actuated by a manual or automatic switch or switch system and that has a power cell coupled to a motor assembly to assist with actuation and firing of the staples.

In another embodiment, the stapler has a power supply that can actuate the stapler and the power source can easily move the drive mechanism to an appropriate position for the next stapling operation.

According to another aspect of the present disclosure, there is provided a surgical stapler. The stapler has a handle assembly including a trigger and a clamping device including a staple cartridge with a plurality of staples and an anvil having a fastener forming surface thereon. The stapler also has a controller configured to determine an occurrence of clamping by the anvil and the staple cartridge. The controller controls firing of the plurality of staples from the staple cartridge. When the trigger is actuated the controller delays firing of the plurality of staples from the staple cartridge to provide for a predetermined time period of tissue compression of the tissue between the anvil and staple cartridge. The controller outputs a control signal to allow firing once the predetermined time period is reached. The stapler also has a motor having a geared assembly. The motor is disposed in the handle and configured to receive the control signal from the controller. The motor is operatively connected to the staple cartridge to fire the staples from the staple cartridge once the control signal is received.

It would additionally be advantageous to provide a surgical stapler having a timer device or display that would allow the surgeon to easily determine an appropriate compression time interval. It would be further advantageous to provide a surgical stapler with a mechanical digital or analog display to allow the surgeon to decide the optimal compression time, then actuate the stapler, insuring more uniformly shaped staples. It would still be further advantageous to provide a surgical stapler with an automatic delay mechanism that, once the trigger is actuated, would fire the stapler after the predetermined amount of time elapses to allow for the required tissue compression. It would still be further advantageous to provide a surgical stapler with a controller that measures one or more parameters (i.e. thickness) of the tissue or stapler to provide the necessary tissue compression with the parameters being selected from the group consisting of motor speed, a gear reduction, or motor actuation time, motor rotation or other mechanical member travel distance and any combinations thereof.

According to a first aspect of the present disclosure, the surgical stapler that has a motor that drives a firing mechanism component of various mechanical components that will manipulate an actuator at a complementary speed to ensure tissue compression and provide for a uniform staple formation.

According to another aspect of the present disclosure, the surgical stapler has a controller to place a delay between actuation of the firing mechanism component and actual firing of the staple.

According to another aspect of the present disclosure, the surgical stapler has a control device that controls a stroke parameter, a distance parameter and/or a time parameter of a firing mechanism component to increase a tissue compression time of the approximation device.

According to still another aspect of the present disclosure, the surgical stapler has a motor and a first switch. The first switch is connected to a motor and delays the motor from actuating in order to achieve an amount of tissue compression by an approximation device. The surgical stapler may have a second switch. The second switch senses another location of a drive screw and actuates a reverse function of the motor to return the drive screw to an initial position.

According to still yet another aspect of the present disclosure, the surgical stapler has an indicator that measure a distance traveled of the drive screw or a tissue compression time of the approximation device.

According to still another aspect of the present disclosure, the surgical stapler has a visual indicator that indicates a position of the firing mechanism component or indicates a status condition of the surgical stapling.

According to a further aspect of the present disclosure, a powered endoscopic surgical apparatus is provided. The surgical apparatus includes a handle including a housing, a power source supported in the housing; an endoscopic portion extending distally from the housing of the handle; a fastening assembly coupled to a distal end of the endoscopic portion, the fastening assembly including a pair of jaws defining a stapling mechanism, at least one of the jaws being movable with respect to the other jaw; a firing member extending between the handle and the fastening assembly; a drive source proximal of the endoscopic portion, the drive source including a motor powered by the power source and connected to the firing member; and a gear assembly engaged with the drive shaft of the motor, the gear assembly being disposed within the housing. The gear assembly includes a gear rack provided on the firing member; and a main gear operatively connected with the gear rack of the firing member, the motor being adapted and configured to spin the main gear such that rotary motion of the main gear moves the firing member linearly in an axial direction such that a distal end of the firing member engages and actuates the stapling mechanism in the fastening assembly.

According to yet another embodiment of the present disclosure, a powered endoscopic surgical apparatus is provided and includes a handle including a housing, a power source supported in the housing; an endoscopic portion extending distally from the housing of the handle; an end effector assembly coupled to a distal end of the endoscopic portion, the end effector assembly including a pair of jaws configured to perform a surgical function, at least one of the jaws being movable with respect to the other jaw; a driving member extending between the handle and the end effector assembly; a drive source proximal of the endoscopic portion, the drive source including a motor powered by the power source and connected to the driving member; and a gear assembly engaged with the drive shaft of the motor, the gear assembly being disposed within the housing. The gear assembly includes a gear rack provided on the driving member; and a main gear operatively connected with the gear rack of the driving member, the motor being adapted and configured to spin the main gear such that rotary motion of the main gear moves the driving member linearly in an axial direction such that a distal end of the driving member actuates the end effector to perform the surgical function.

The end effector may be a stapling mechanism and the surgical function may include a stapling function. In use, linear movement of the driving member may actuate the end effector to perform a fastening function.

The main gear may be a spur gear. The gear rack may be formed along a bottom surface of the firing member.

The handle may further include a manually actuated closing lever supported on the housing; and a closure member having a proximal end operatively connected to the closing lever and a distal end extending through the endoscopic portion to the fastening assembly, wherein manual actuation of the lever imparts linear movement of the closure member in an axial direction such that the distal end of the closure member engages and actuates the fastening assembly to open and close the pair of jaws.

The handle may further include a trigger supported on the housing, wherein the trigger is operatively connected to the power source, the power source being operatively connected to the motor of the drive source such that manipulation of the trigger actuates the power source to activate the motor and rotate the main gear to actuate the firing member.

The endoscopic surgical apparatus may further include a controller configured to control the motor, the controller delaying activation of the motor for a predetermined time period after actuation of the lever.

The predetermined time period may be suitable in length to allow compression of the tissue for the predetermined time period and to allow tissue to settle from a first initial state into a second compressed state when the pair of jaws are in a closed position.

The endoscopic surgical apparatus may further include a dampening device, the controller configured to control the dampening device, the dampening device modulating the motor for the predetermined time period to allow for compression of tissue when the pair of jaws are in a closed position.

The controller may control the motor and may delay an actuation thereof, the delay permitting a predetermined compression time period when the pair of jaws are in a closed position.

The controller may slow an operation of the motor to provide for the delay to compress the tissue.

The handle may include a switch supported on the housing, wherein the lever actuates the switch upon actuation thereof, wherein the switch, when actuated, outputs a signal to the controller to complete a suitable timer circuit for a predetermined time interval.

In use, upon passage of the predetermined time interval, actuation of the motor may be permitted.

The power source may be a battery. The battery may be modular.

DESCRIPTION OF THE DRAWINGS

Other and further objects, advantages and features of the present disclosure will be understood by reference to the following specification in conjunction with the accompanying drawings, in which like reference characters denote like elements of structure and:

FIG. 1 A is a schematic of the handle portion of the surgical stapler of FIG. 1 showing the trigger switch and a power cell coupled to a motor;

DETAILED DESCRIPTION

Figure 1:
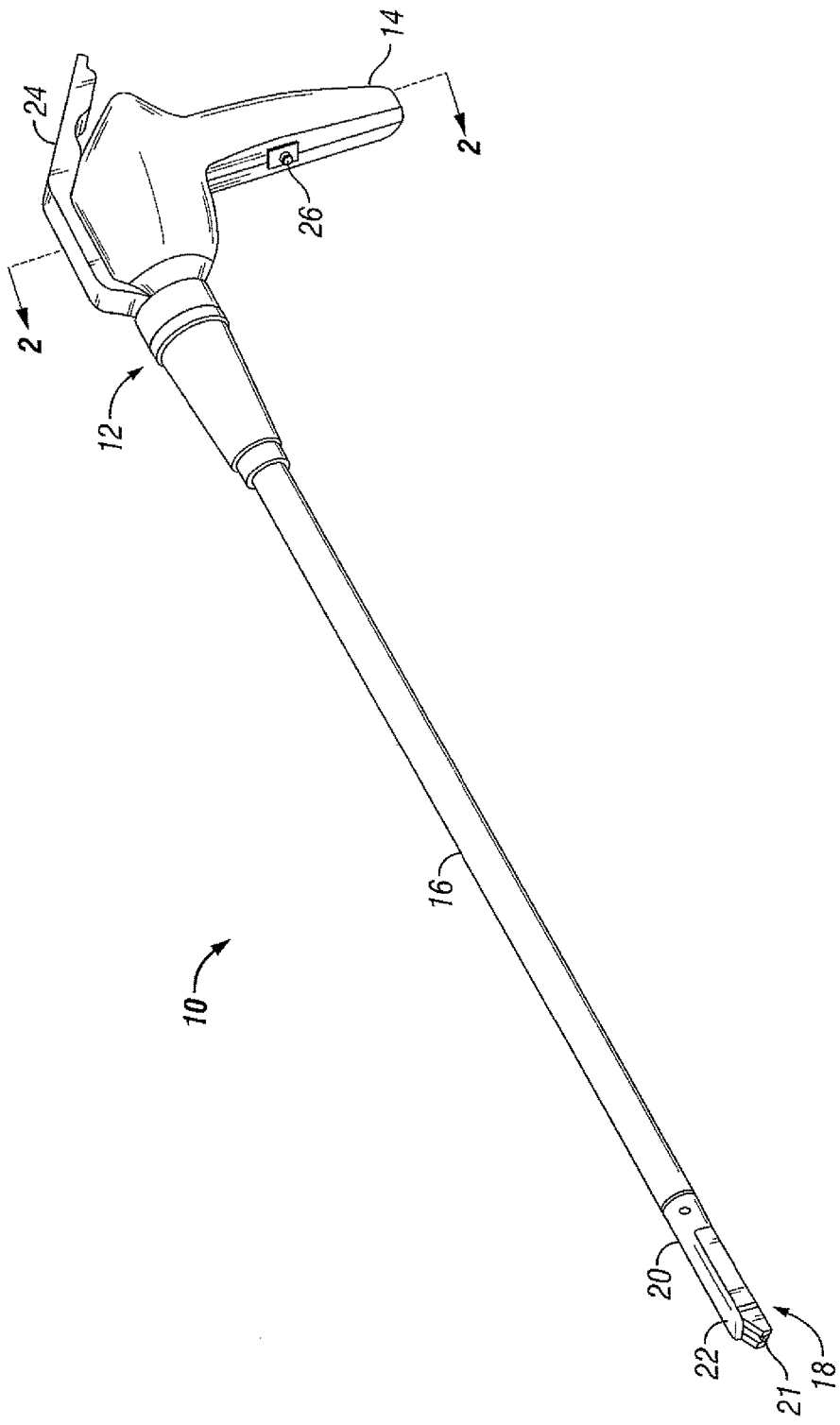
FIG. 1 is a perspective view of a first embodiment of a surgical stapler of the present disclosure.
Figure 1A:
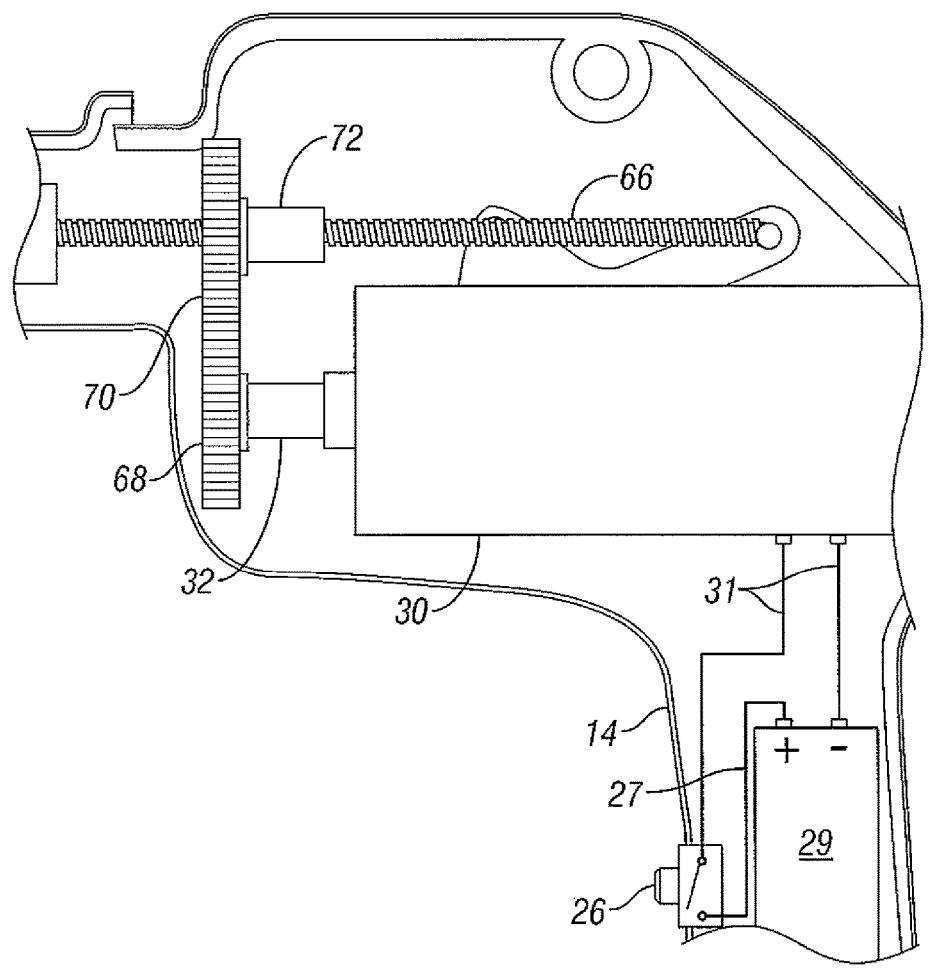

In the drawings and in the description which follows, the term "proximal", as is traditional, will refer to the end of the apparatus which is closest to the operator, while the term "distal" will refer to the end of the apparatus which is furthest from the operator.

The present disclosure shall be discussed in terms of both conventional and endoscopic procedures and apparatus. However, use herein of terms such as "endoscopic", "endoscopically", and "endoscopic portion", among others, should not be construed to limit the present disclosure to an apparatus for use only in conjunction with an endoscopic tube. To the contrary, it is believed that the apparatus of present disclosure may find use in procedures in these and other uses including but not limited to where access is limited to a small incision such as arthroscopic and/or laparoscopic procedures, or any other conventional medical procedures known in the art.

The present disclosure may also be used with surgical stapling devices that do not have any separate clamping and firing procedures and may be used with such surgical stapling devices having a simultaneous clamping and firing. The present disclosure is also intended to be used with such surgical stapling devices have a discrete clamping gradient.

Referring now to the figures, wherein like reference numerals identify similar structural elements of the subject disclosure, there is illustrated in FIG. 1 a self-contained powered surgical stapler constructed in accordance with one embodiment of the subject disclosure and designated generally by reference numeral 10. The surgical stapler 10 is a disposable surgical instrument. However, the disposable arrangement is non-limiting and other non-disposable arrangements may be contemplated and are within the scope of the present disclosure.

The surgical stapler 10 of the present disclosure shown in a perspective view in FIG. 1 and described herein includes a frame generally represented by reference numeral 12 and handle generally represented by reference numeral 14. The frame 12 defines a series of internal chambers or spaces for supporting various mechanical components of the surgical stapler 10 as well as a number of staples therein for the application to the body tissue.

The frame 12 supports an endoscopic portion 16 or an extended tube-like portion. The endoscopic portion 16 is capable of being rotated and has a relatively narrow diameter, on the order of in a range that includes about 10 millimeters, and is for insertion into a small opening in or tube inserted into the body, such as in the abdominal cavity, or other similar body cavities. The endoscopic portion 16 has a longitudinal axis and has a length. The length is appropriate for reaching the operation site in the interior of the body. The surgical stapler 10 may be used in conjunction with other instruments such as endoscopes or other such optical devices for visually examining the interior of the body, for example, cameras by means of fiber optics or other optical or recording devices.

Generally, the endoscopic portion 16 of the surgical stapler 10 is inserted through the small opening or wound, and is manipulated to the operation site. At the operation site, the surgical stapler 10 is actuated.

The endoscopic portion 16 has a fastening assembly 18 and cutting assembly that is known in the art. The fastening assembly 18 and the cutting assembly are located in a housing 20 which carries a fastener and a cutter to the operation site. The fastening assembly 18 in this one non-limiting embodiment has a pair of jaws 21, 22, or an anvil 22 and a staple cartridge 21. The jaws 21, 22 may be a first jaw 21 and second jaw 22 that opens and closes or alternatively another clamping structure for compression of the tissue at the stapling site. The jaws 21,22 are defined by a staple carrying cartridge 21 and the anvil 22 that is located therein. The staple carrying cartridge 21 is in one embodiment located at the distal end of the housing 20. The staple carrying cartridge 21 has one or a number of rows of staples. The surgical stapler 10 also has an anvil 22 with a forming surface (not shown) and further includes a knife (not shown) as is well known in the art for accomplishing the surgical stapling.

Generally, actuating the operating portion of the fastening assembly 18 is accomplished via intermediate components disposed on or within the narrow longitudinally extending tubular endoscopic portion 16. In one embodiment, a cylindrical tubular sleeve member surrounds the endoscopic portion 16. The sleeve may be manipulated in a direction with the longitudinal axis of the surgical stapling device. The surgical stapler 10 of the present disclosure has three basic actions or functions.

First, the endoscopic portion 16 is introduced into the human or animal body and is positioned with the jaws 21,22 aligned at the desired stapling site to receive the target tissue. This may involve rotation of the endoscopic portion 16 relative to the body, either by rotating the surgical stapler 10, as a whole, by rotating simply the endoscopic portion 16 relative to the frame 12 as permitted, or a combination of both actions. Thereafter, the surgical stapler 10 secures the target body tissue between the staple cartridge 21 in the distal portion of the housing 20 and the anvil 22. This is accomplished by a clamping action of the jaws 21, 22 or alternatively by another similar or different clamping member. The jaws 21, 22 are allowed to remain in the closed position for a period of time. The jaws 21, 22 remaining closed for a predetermined period of time allow any excess liquid or fluid in the tissues to drain out of the body tissues prior to actuation of the stapling mechanism. This ensures that the liquid does not rapidly traverse out of the tissues to impede formation of the closed or formed staple and ensures a proper staple formation.

With the target tissue clamped between the anvil 22 and the staple cartridge 21, a camming surface which surrounds the housing 20 and anvil member 22 may be employed to close the jaws 21, 22 of the surgical stapler 10 and clamp the tissue between the anvil 22 and the tissue contacting surface of the staple cartridge 21. The jaws 21, 22 may be clamped by actuating or closing lever 24 that is opposite the jaws 21, 22. Thereafter, the third action of the operator or more particularly the surgeon is that of applying the staples to the body tissue. A longitudinally extending channel is employed to deliver longitudinal motion to an axial drive member and a tissue cutting knife.

The stapler 10 may have an axial drive member or an axial drive screw to contact a pusher. The pusher elements drive the staples through the body tissue against the fastener or forming surface of the anvil 22. Typically, in the art the surgical stapler 10 fires usually by an actuation of a first trigger 26. Thereafter, the clamping action of the jaws 21, 22 is released and the surgical stapler 10 or a portion thereof may be withdrawn from the body cavity or site.

A known and recognized benefit is that often an operator will desire a surgical stapler 10 that is self-actuating or that actuates with only a limited degree of physical force using the trigger handle (not shown) or using a trigger switch 26. It is envisioned that surgeons would desire such a surgical stapler 10 that does not have to be connected to any external power supply but instead includes an internal battery operated power supply. Operators would desire a surgical stapler having an internal power source that is comfortable to hold, compact and that is very suitable for endoscopic or laparoscopic procedures as well as other conventional surgical procedures. The stapler 10 of the present disclosure is advantageous since it is a compact and ergonomic member. It is also very advantageous to form such a surgical stapler 10 from few component parts relative to the prior art surgical instruments. This reduces manufacturing costs of the surgical stapler.

The present disclosure in one embodiment uses a motor drive source having a substantially offset or a direct drive to remedy these known issues in the art. FIG. 1 A shows a schematic illustration of an interior of the handle 14. The surgical stapler 10 in this embodiment is powered by a motor 30. The trigger switch 26 in this embodiment is connected by lead 27 to a power source 29 such to as a battery. The battery 29 is connected by lead 31 to a motor 30. The motor is connected by lead 31 to the switch 26. Upon the actuation of switch 26, power will traverse from the battery 29 to the motor 30. The energized motor 30 will rotate the motor drive shaft 32 to spin gear 68. Gear 68 is in contact with gear 70. Gear 68 rotates second gear 70 which will rotate drive screw 66. The drive screw 66 upon rotation will move in a longitudinal manner to actuate one or more other components of the surgical stapler 10 such for compression of tissue or stapling. Although, the battery 29 and the motor 30 are shown as being located in the handle 14, other locations are contemplated.

Figure 2:
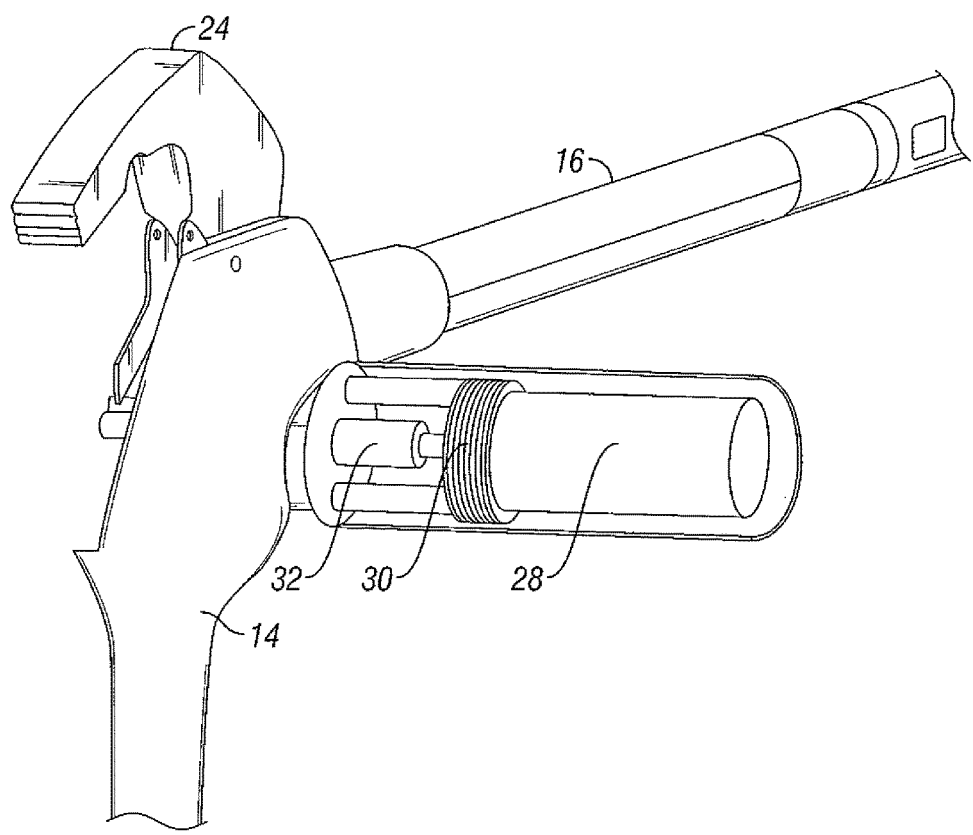
FIG. 2 is an exterior cross sectional view of the surgical stapler along line 2-2 of FIG. 1 with the surgical stapler having a drive compartment thereon.

Referring now to FIG. 2, there is shown a cross sectional view of the surgical stapler 10 of the present disclosure along line 2-2 of FIG. 1 from a rear view of the surgical stapler of FIG. 1. Disposed on an adjacent side of the surgical stapler 10 is shown a protective housing 28. The protective housing 28 is for housing one or more components of the surgical stapler 10. The protective housing 28 may be disposed on either adjacent side of the handle 14 or in another position being parallel with the handle. The protective housing 28 is a generally a cylindrical compact member having an interior that is disposed adjacent to, and on a lateral side of the handle 14. The protective housing 28 is made from a suitable thermoplastic member that is suitable for surgical procedures and has a suitable volume to hold one or more commercially available batteries, or another power source. Although shown as cylindrical, other shapes are possible and the protective housing 28 is not limited to this configuration. The protective housing 28 has the interior space. The space has a compact size and has an advantageous drive source 30 disposed therein.

The surgical stapler 10 of the present disclosure may have a first axial drive shaft for operation of the stapling mechanism in the proximal end of the surgical stapler 10 as is known in the art. Such stapling mechanisms are well known in the art and may be found in U.S. Pat. No. 6,330,965 B1 to Milliman, et al., U.S. Pat. No. 6,250,532 B1 to Green, et al., U.S. Pat. No. 6,241,139 B1 to Milliman, et al., U.S. Pat. No. 6,109,500 to Alli et al., U.S. Pat. No. 6,202,914 B1 to Geiste, et al., U.S. Pat. No. 6,032,849 to Mastri, et al. and U.S. Pat. No. 5,954,259 to Viola, et al., which are all herein incorporated by reference in their entirety.

The drive source 30 has electrical contacts to an integrated power supply and an optional switch system. The drive source 30 is run by any integrated power supply that is compact, and low cost to manufacture. In one embodiment, the drive source 30 also has a suitable amount of torque in order to fire and apply the staple to the body tissue or bone, and form the staple using a forming surface disposed on an anvil. In one embodiment, the drive source 30 is a simple motor assembly having a drive shaft 32. The motor may be any device that converts the current from the portable power cells into mechanical energy but may be any motor that is low cost and that may be disposable and easily discarded after use. The drive shaft 32 is connected through the handle 14 through a sealed aperture in the handle 14. Aperture may be sealed using an "O" ring or similar structure to ensure no fluids enter the stapler 10.

Alternatively, the drive source 30 may comprise any electrically powered motor known in the art. The present disclosure provides that the drive source 30 may have a number of modular components that are disposable, permanent, replaceable or interchangeable. In one aspect, the motor 30 may be a modular component and replaceable. In another aspect, the battery can be a modular component and replaceable separate from the drive source 30. In still another aspect, both the battery and the motor of the drive source 30 may be modular components. The motor and battery may be stored in a casing or be separate units.

In one embodiment, the drive source 30 has electrical contacts to, and is powered by, one more internal power cells. The power cells may be one or more disposable or rechargeable power cells. For example, the power cells may be a nickel cadmium type battery, an alkaline battery, a lithium battery, or a nickel metal hydride and may be replaceable or disposable with the entire surgical stapler 10. Alternatively, the power cells of the drive source 30 may also 5 disengage from the surgical stapler 10 for recharging. Once disconnected, the surgical stapler 10 itself then may be discarded after use.

In one embodiment, the one or more power cells of the drive source 30 are disposed and oriented in a generally perpendicular fashion relative to an 10 outer surface of the handle 14 as shown in the housing 28 and optionally may be located in a casing with the motor assembly. In this non-limiting embodiment, the surgical stapler 10 may have a discrete analog switch assembly to actuate the drive source. The switch assembly may be located in any location or on an external surface of the surgical stapler 10, or be integral with the trigger switch 26. Alternatively, the drive source 30 may be actuated by a counter clockwise rotation of the protective housing 28 to actuate the drive source. Still further in another embodiment, the drive source 30 may be actuated by the trigger 26 or by simply the lowering an elevation of the lever 24.

Figure 3:
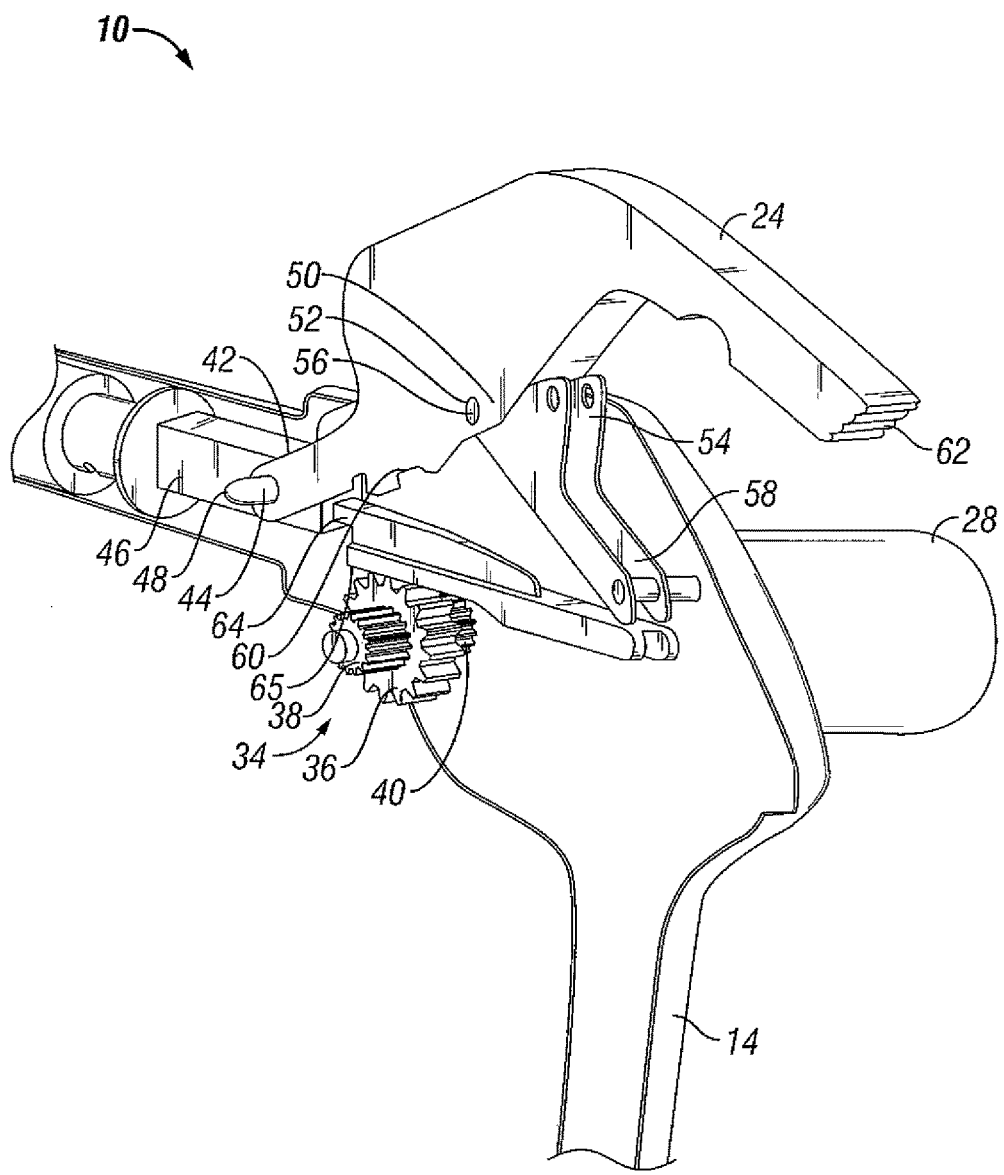
FIG. 3 is an interior cross sectional view of the surgical stapler being opposite the compartment.

Referring now to FIG. 3, there is shown an opposite lateral side cross-sectional view of the surgical stapler 10 of FIG. 2, having the lever 24 in an elevated position or elevated and away from the handle 14. The drive shaft 32 of the drive source 30 extends through the lateral side wall of the handle 14 and engages a gear assembly 34. The gear assembly 34 may have any number of gears to transmit motion from the drive source 30 in protective housing 28 to another member to move a suitable driving member for stapling. The driving member is a gear rack or drive screw or other member to fire the staples in the staple cartridge 21. Various driving configuration are possible and the present stapler 10 is not limited to any such particular driving arrangement. In this one non-limiting embodiment, the gear assembly 34 has a main gear 36 and two subordinate gears 38, 40. The gear assembly 34 laterally extends into the interior space of the handle 14 as shown. In one embodiment, the gear 36 is a spur gear. In one embodiment, the subordinate gears 38, 40 are a pair of pinion gears. In yet another embodiment, instead of a pair of pinion gears 38, 40, the stapler 10 may have one pinion gear. Various gearing configurations are possible and within the scope of the present disclosure.

The lever 24 as shown has a first lever side 42 that has a transverse aperture 44 being disposed therethrough. The lever 24 is connected to a member 46 by a link pin 48 through aperture 44 in the lever 24. The member 46 moves laterally through the endoscopic portion 16. The member 46 controls the jaws 21, 22 shown in FIG. 1 to open or close and for the surgeon to clamp the jaws of the surgical stapler 10 on or at the desired tissue site. The lever 24 also has an intermediate portion 50. The intermediate portion 50 has a second aperture 52 being disposed in a bottom side of the lever 24. The lever 24 is further connected to a second linkage assembly 54 through the second aperture 52 by a second link pin 56. It should be appreciated that the powered arrangement is not limited to any such device that requires tissue approximation such as a TA surgical stapler such as U.S. Pat. No. 6,817,508 to Racenet, et al. which is herein incorporated by reference in its entirety, and the powered arrangement may encompass other staplers that do not require any such tissue approximation prior to firing.

In one embodiment, the second linkage assembly 54 has two discrete links. Each of the links is spaced apart and is connected to one another to form an integral second linkage assembly 54. The second linkage assembly 54 is for translating a downward force from the lever 24 into an axial lateral force and for moving one or more structures in the handle 14. The second linkage assembly 54 is further fixedly connected to an interior pin 58 of the handle 14. The lever 24 still further has an orthogonal notch 60. The notch 60 is disposed on the lever 24 with the notch being between the transverse aperture 44 and the second aperture 52. The notch 60 provides clearance and prevents the lever 24 from interfering or otherwise contacting the gear assembly 34 during a firing sequence or otherwise when the drive source 30 is actuated.

As shown in the raised position, the free end 62 of the lever 24 rests elevated above the handle 14 as shown. As mentioned, when a stapling site is determined by the operator, the operator will use the jaws 21, 22 to compress the tissue at the stapling site to clamp the tissue for a period of time. The surgeon can control the jaws by lowering or closing lever 24 (from the elevated position to a position that rests on the handle 14). Upon lowering the lever 24 from the elevated position above the handle 14, the lever 24 lowers the second linkage assembly 54.

The second linkage assembly 54 forces the lever 24 at the first side 42 to move the member 46. The member 46 is then manipulated in a lateral axial direction opposite the handle 14. Thus, member 46 drives the jaws 21, 22 at the distal side of the surgical stapler 10 for clamping the selected body tissue between the jaws. In one embodiment, the member 46 may further contact a lead, switch or mechanical member in order to provide an audible or visual alert so as to inform the physician/operator that a preset period of time has elapsed for compression of tissue between the jaws and the firing can begin. Various clamp arrangements are possible and the present arrangement is for illustration purposes as it is envisioned that the clamp may be powered by the drive source 30, or by a separate drive source.

In another embodiment of the surgical stapler 10, the surgical stapler 10 may be manually actuated for stapling. In the manual embodiment, when the desired stapling is desired, the operator will actuate either a trigger handle (not shown) or in another embodiment will actuate a handle assembly having a linkage. Still in another embodiment, the lever 24 may operate the switch assembly at an end of the lever 24. The switch assembly 26 may be on any location of the surgical stapler 10 or may be adjacent to the protective housing 28.

The surgical stapler 10 further has a firing member 64. The firing member 64 is laterally disposed in the handle 14 and can optionally assist with driving an axial drive screw or another driving member to actuate the stapling mechanism in the distal side of the surgical stapler 10. The firing member 64 may include a single driving member that can control both the clamping and the firing of the surgical stapler 10. In another embodiment, the firing member 64 can alternatively include separate driving members with one driving member for the firing of the stapler cartridge 21 and another driving member for closing the jaws 21, 22. Various configurations are possible and within the scope of the present disclosure. The firing member 64 is a longitudinal member having a bottom driving surface 65. However, the longitudinal firing member 64 can be a single component or constructed of other multiple members. The firing member 64 is disposed in a longitudinal manner in the interior of the handle 14 of the surgical stapler 10. Upon actuation, the motor in the housing 28 spins the main gear 36 that contacts or is connected to the bottom driving surface 65 of the firing member 64. Gear 36 rotates in a counterclockwise fashion. Thus, in this manner, the drive source 30 will rotate the gear assembly 34 that will move the firing member 64 in an axial direction toward the distal direction of the surgical device 10 and away from the handle 14. A rotation of the main gear 36 applies a force to the firing member 64 on the bottom driving surface 65 for the purpose of axially moving the firing member in a longitudinal distal manner. This axial movement of the firing member 64 will impart an axial force the corresponding member in the endoscopic portion 16 that will engage the stapling mechanism.

A beneficial aspect of the present disclosure is that the drive source 30 will then allow a greater amount of torque to be applied to the driving member 64 relative to a manually actuated apparatus without any motor assembly 30. A significant aspect of the present disclosure is that the drive source or motor 30 is a low cost device that may be discarded. Given that the drive source 30 may be discarded, the drive source or motor 30 may be connected to an optional analog or digital circuit on a controller to drive the firing member 64 with a predetermined amount of torque so that a considerable amount of power is released from the drive source 30 each instance the firing is desired. Moreover, the surgical stapler 10 provides that the firing member 64 is directly driven by the drive source 30, or geared by a number of gears for the purpose of actuating the stapling mechanism without undue force or movement applied to the handle 14 or another trigger handle (not shown) of the surgical stapler 10. This is advantageous since the surgeon can precisely locate the stapler 10 at a site and then fire the stapler 10.

Figure 3A:
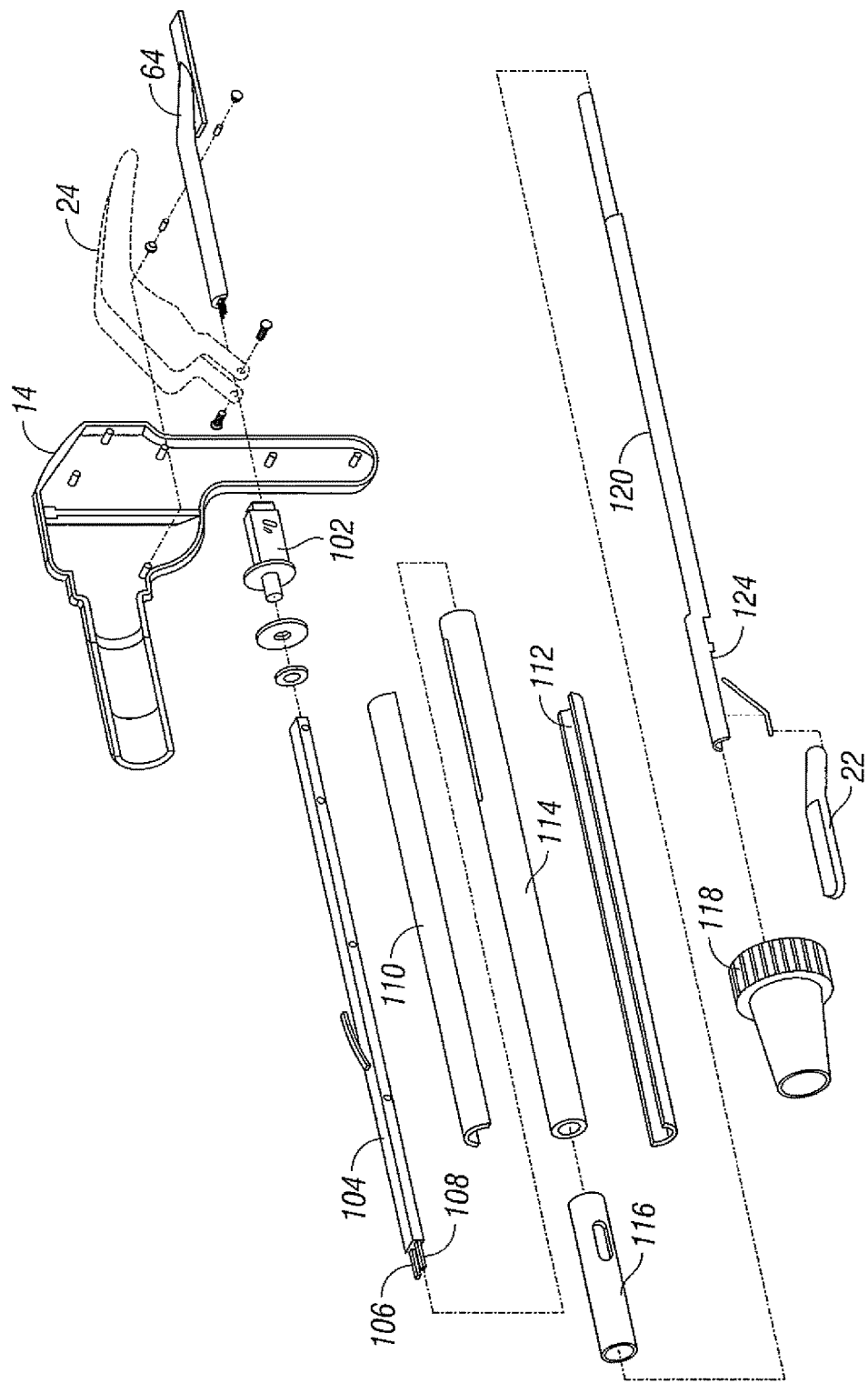
FIG. 3A is an exploded view of a channel of the surgical stapler of one embodiment of the stapler.

FIG. 3A shows an exploded view of a number of components of the surgical stapler 10 of FIG. 1. The stapler 10 has a rack 64 that is slidable in the handle portion 14. The rack 64 interfaces with a clamp tube 102. On a distal side of the clamp tube 102 is a channel 104. The channel 104 engages with the clamp tube 102 and a pair of forks 106,108 on a distal side thereof. The stapler 10 also has an upper cover 110 and a lower cover 112, and an extension tube 114. The extension tube 114 engages with a collar tube 116. The stapler 10 also has a rotation knob 118 with a channel portion 120. The channel portion 120 has a pair of camming surfaces 122 on a distal end. The distal end also has a crimp 124 in a distal side to receive the anvil 22.

In operation, the rack 64 slides and moves the clamp tube 102 distally. The clamp tube 102 is provided to interconnect the handle portion 14 arid the extension tube 114. The channel 104 is slidably mounted for reciprocal longitudinal motion. The extension tube 114 provides support for the surgical stapler 10 and has slots that interface with the collar tube 116. The surgical stapler 10 also has a support 120 for longitudinal motion and to operate the stapling mechanism as described in FIG. 2b. The operation of these components is well known and is disclosed in U.S. Pat. No. 5,318,221 to Green, et al., which is herein incorporated by reference in its entirety.

Figure 3B:
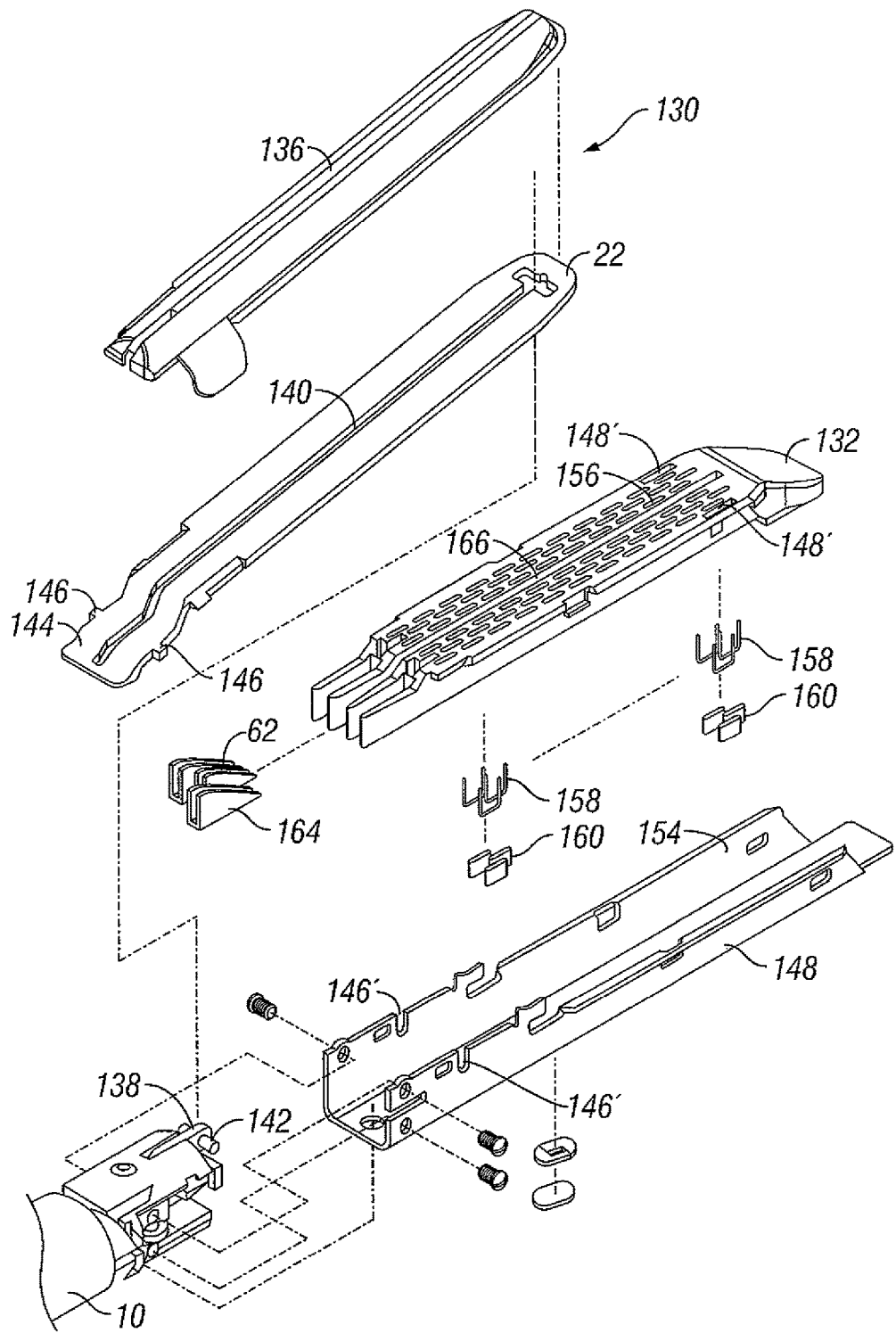
FIG. 3B is an exploded view of the staple cartridge, anvil and the drive sled of FIG. 1.

Advantageously, the rack 64 is driven distally to advance the channel 104 in a distal manner. The channel 104 delivers longitudinal motion to a pusher cam bar or an axial drive member as is known in the art for operation of the staple cartridge 21 shown in FIG. 2b. It should be appreciated that the components shown in FIG. 3A only illustrate one embodiment of the present surgical stapler 10, and instead of the rack 64, the surgical stapler 10 may have a drive screw (FIG. 4) for longitudinal motion and in order to actuate the staple cartridge 21. Referring now to FIG. 3B, there is shown an exploded view of the anvil 22 and the staple cartridge 132 having an actuation sled 169.

Referring to FIG. 2b, the staple cartridge 21 includes an anvil assembly 130 and a cartridge assembly 132 shown in an exploded view for illustration purposes. The anvil assembly 130 includes anvil portion 22 having a plurality of staple deforming concavities (not shown) and a cover plate 136 secured to a top 10 surface of anvil portion 134 to define a cavity (not shown). The cover plate 136 prevents pinching of tissue during clamping and firing of the surgical stapler 10. The cavity is dimensioned to receive a distal end of an axial drive assembly 138.

The anvil 130 has a longitudinal slot 140 that extends through anvil portion 130 to facilitate passage of retention flange 142 of the axial drive assembly 138 into the anvil slot 140. A camming surface 144 formed on anvil portion 22 is positioned to engage axial drive assembly 138 to facilitate clamping of tissue. A pair of pivot members 146 formed on anvil portion 130 is positioned within slots 146' formed in carrier 148 to guide the anvil portion 130 between the open and 20 clamped positions.

The stapler 10 has a pair of stabilizing members 152 engage a respective shoulder formed on carrier 148 to prevent anvil portion 130 from sliding axially relative to staple cartridge 132 as camming surface of the anvil 130 is deformed. Cartridge assembly 132 includes the carrier 148 which defines an elongated support channel 154. Elongated support channel 154 is dimensioned and configured to receive the staple cartridge 132 which is shown above the carrier 148 in the exploded view of FIG. 2b. Corresponding tabs and slots formed along staple cartridge 132 and elongated support channel 148' function to retain staple cartridge 132 within support channel 154 of carrier 148. A pair of support struts formed on the staple cartridge 132 are positioned to rest on side walls of carrier 148 to further stabilize staple cartridge 132 within support channel 154, however to other arrangements to support the cartridge 132 on the channel 154 can be used and this arrangement is not limiting.

Staple cartridge 132 includes retention slots 156 for receiving a plurality of fasteners 158 and pushers 160. Longitudinal slots 156 extend through staple cartridge 132 to accommodate upstanding cam wedges 162 of the actuation sled 164. A central longitudinal slot 166 extends along the length of staple cartridge 132 to facilitate passage of a knife blade (not shown). During operation of surgical stapler 10, actuation sled 164 is drive distally to translate through longitudinal slot 156 of staple cartridge 132 and to advance cam wedges 162 distally and into sequential contact with pushers 160, to cause pushers 160 to translate vertically within slots 156 and urge fasteners 158 from slots 156 into the staple deforming cavities of anvil assembly 130 to effect the stapling of tissue.

Figure 4:
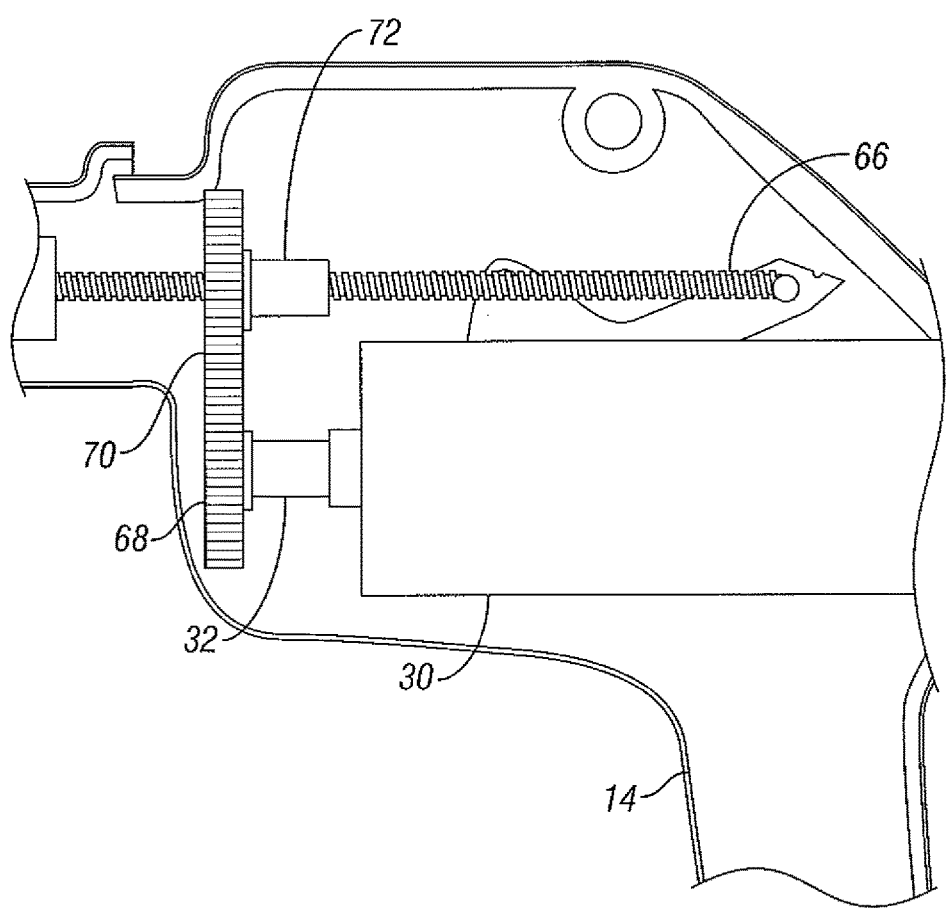
FIG. 4 is another cross sectional view of another embodiment of the surgical stapler of FIG. 1 having a drive source in the handle of the surgical stapler.

Referring now to FIG. 4, there is shown another embodiment of the present disclosure. In this embodiment, the drive source 30 is disposed in an interior space of the handle 14 in a location to balance an overall weight of the surgical stapler 10 for a more ergonomic, comfortable design. The surgical stapler 10, in this embodiment, has a drive screw 66 as a drive member in contrast to the rack 64 of FIG. 3A. The drive screw 66 is a threaded rod having a number of helical grooves that are intended to rotate and contact another axial member shown above to actuate the stapling mechanism in the distal location of the surgical stapler 10 once a tissue compression is made by the surgeon. Various configurations are possible, and it should be appreciated that the stapler 10 of the present disclosure is not intended to be limited to any specific stapler mechanism.

In one embodiment, the drive source 30 is disposed and lies in a longitudinal plane in the handle 14. The drive source 30 is disposed substantially parallel to a longitudinal axis of the surgical stapler 10. This location of the drive source 30 provides for a compact and self powered surgical stapler 10 that may be comfortably balanced and ergonomically grasped by the surgeon. The drive source 30 has the drive shaft 32. Drive shaft 32 is connected to a first drive gear 68. The first drive gear 68 has teeth that mesh with, and rotate a number of teeth of a second translating gear 70 as shown.

The second translating gear 70 further has a bore or aperture in a center of the second translating gear 70. The second translating gear 70 further is connected to a collar 72 in a center of the second translating gear. The collar 72 engages the drive screw 66 of the surgical stapler 10. A clockwise rotation of the second translating gear 70 will also rotate the collar 72 in a similar direction. The collar 72 will then, upon rotation, cooperates and engage with the drive screw 66 to move the drive screw 66 in a distal manner.

This rotation of the collar 72 allows the drive screw 66 to rotate and move distally. The drive screw 66 rotates and moves in an axial manner through the bore of the second translating gear 70 and the collar in a direction toward and through the endoscopic portion 16 of the surgical stapler 10. Upon rotation, the drive screw 66 will traverse laterally by rotation into the endoscopic portion 16 a predetermined amount in a direction away from the handle 14 of the surgical stapler 10 to actuate the stapler mechanism. A significant aspect of this embodiment is that the drive screw 66 has a considerable amount of torque from motor 30 in order to translate the force to the staple mechanism and to form the staples against anvil.

Figure 4A:
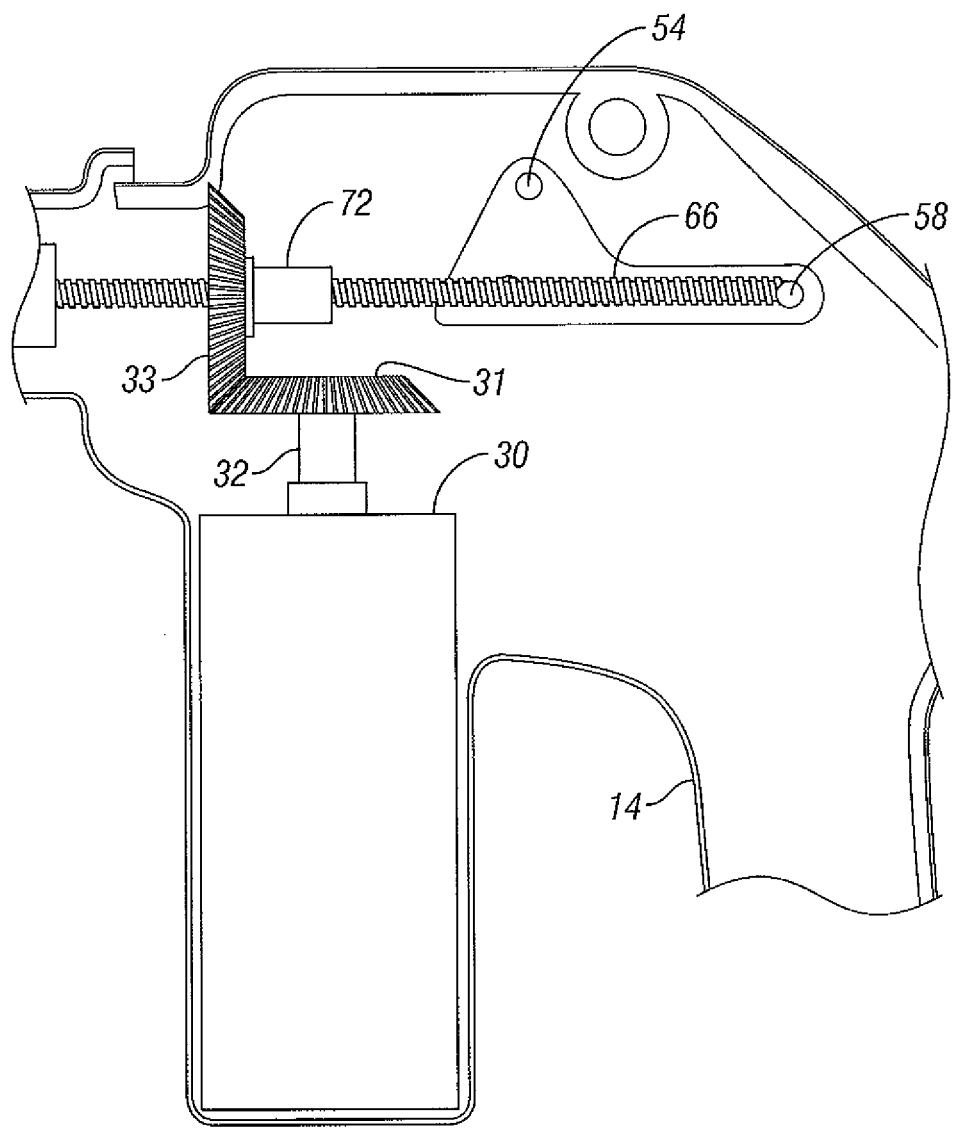
FIG. 4A illustrates another cross sectional view of the surgical stapler of FIG. 1 having a bevel geared arrangement.

FIG. 4A illustrates another embodiment of the surgical stapler 10. In this embodiment, the motor 30 is shown unconnected from any power supply for illustration purposes. The motor 30 has a drive shaft 32. The drive shaft 32 is connected to a first bevel gear 31.

In this embodiment, the motor 30 is disposed at ninety degrees from the drive screw 66. Upon the actuation of trigger switch 26 (FIG. 1) power will traverse from the battery 29 to the motor 30 (FIG. 1 A). The energized motor 30 will rotate the motor drive shaft 32 to spin bevel gear 31. Bevel gear 31 is in contact with second gear 33 that is disposed in concentric fashion with drive screw 66 using member 72 as discussed above.

Bevel gear 31 will rotate drive screw 66 to move the drive screw 66 in a longitudinal manner to actuate one or more other components of the surgical stapler 10 such for tissue compression or for stapling. Bevel gear 31 is useful to change a rotation direction of the motor output shaft 32 to move drive screw 66 longitudinally or distally and proximally, and to orient the motor 30 in an advantageous manner relative to the handle 14. Bevel gear 31 has teeth that can be straight, spiral or hypoid. Although bevel gear 31 is shown as perpendicular to gear 33, other arrangements are contemplated. Instead, of bevel gear 31 with second gear 33 oriented as shown the surgical stapler 10 may incorporate a hypoid gear which can engage with the axes in different planes. Hypoid gear may further permit different spacing arrangements of the motor 30 relative to the drive screw 66 to further provide for a more compact, balanced and ergonomic stapler design.

Figure 5:
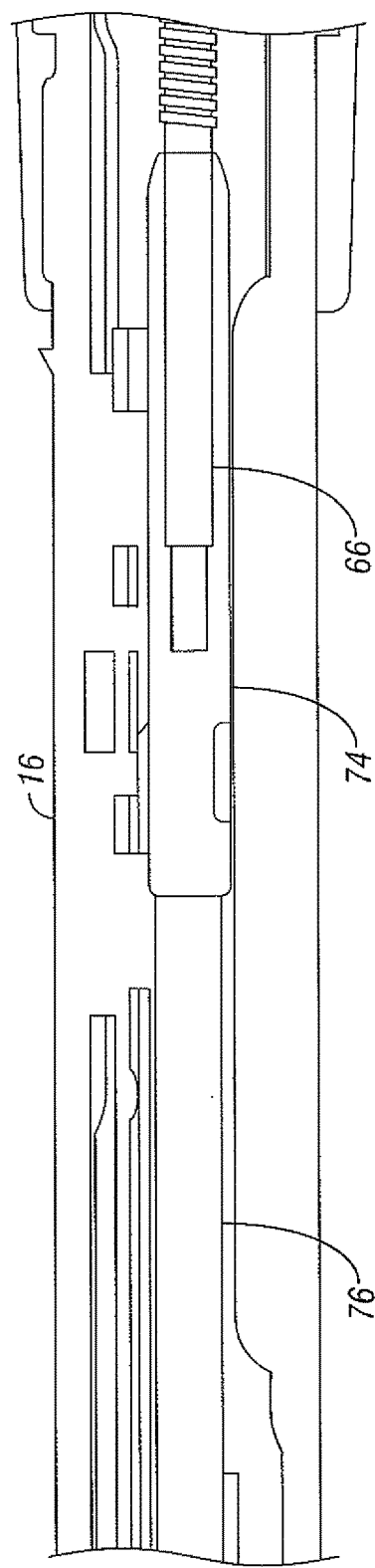
FIG. 5 is a cross sectional view of an endoscopic portion of the surgical stapler of FIG. 4.

Referring now to FIG. 5, there is shown a cross sectional view of the endoscopic device 16. Upon actuation, the drive screw 66 rotates a predetermined distance through a central bore 74 in the endoscopic portion 16. After traversing the predetermined distance, the drive screw 66 will contact a longitudinal firing member 76. The longitudinal firing member 76 will then contact a complementary structure to fire the staples in the staple cartridge 21 in the distal region of the surgical stapler 10 as is known in the art. In another exemplary embodiment, of the present disclosure, the drive source 30 may be a reversible drive source. Additionally, the staple cartridge 21 may have one row to or multiple rows of staples and the surgical stapler 10 may fire with an amount of torque to easily form staples having the desired configuration.

In this alternative embodiment, the drive screw 66 may reverse automatically or manually to move proximally at the conclusion of the stapling relative to the endoscopic portion 16. Upon the drive source 30 actuated by the switch 26 or another manual or automatic actuating device, the drive source rotates the drive shaft 32 in the opposite rotational direction. The drive shaft 32 then rotates the first drive gear 68 in the opposite rotational direction. Thereafter, a number of teeth of the first drive gear 66 rotate the second translating gear 70 in the opposite direction. The second translating gear 70 will then rotate the drive screw 66 in the opposite direction to return the drive screw 68 to an initial position for the next stapling operation.

Figure 6:
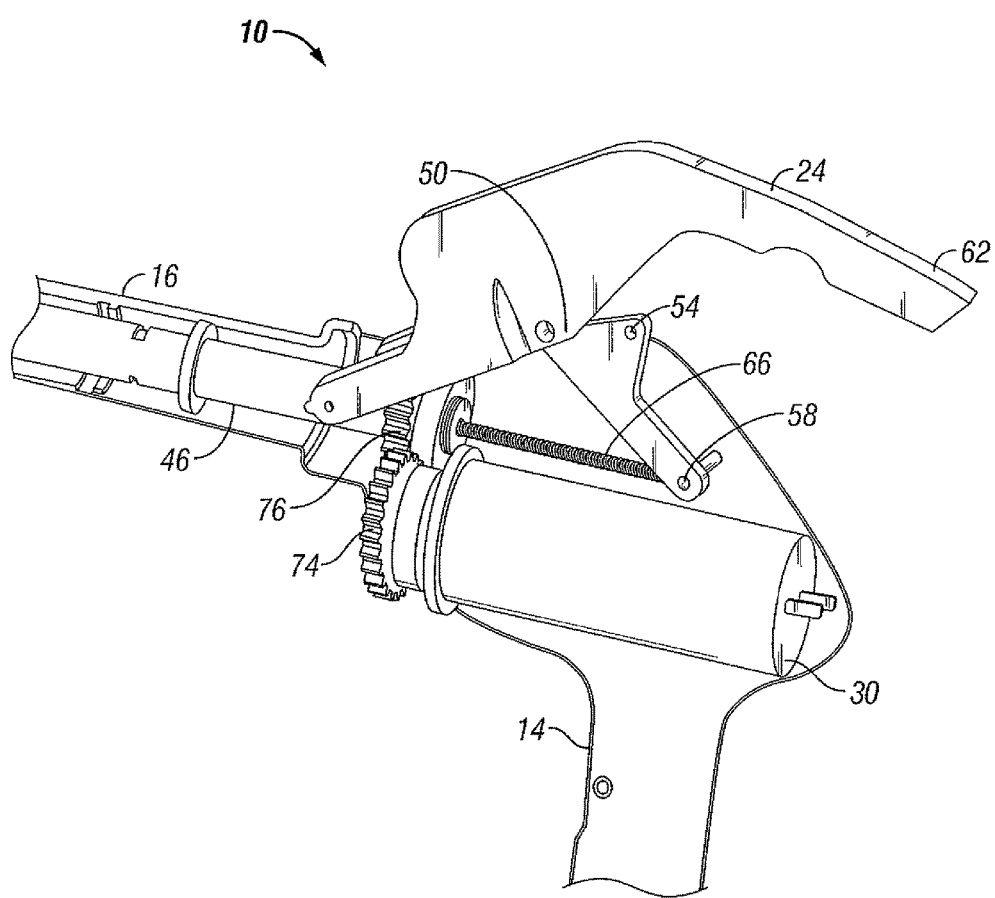
FIG. 6 is yet another cross sectional view of another embodiment of the surgical stapler of FIG. 1 with the drive source being in the handle and geared to the drive screw of the surgical stapler.

Referring now to FIG. 6, there is shown another alternative embodiment of the present disclosure. In this embodiment, the jaws 21, 22 are powered by the drive source 30. The jaws 21, 22 may be moved in close alignment with one another to clamp tissue therebetween and be powered by motor or drive source 30. The surgical stapler 10 has a drive source 30 that has a drive gear 74 being connected to the output drive shaft (not shown) of the motor 30 or drive source. The drive gear 74 is directly connected to the drive source 30, however alternatively may be connected to the drive source 30 by another gear or by another linkage depending on the space constraints of the handle 14. The surgical stapler 10 further has a second translation gear 76. The second translation gear 76 also is connected through the drive screw 66 that drives the drive screw 66 to fire the staple cartridge 21 as discussed previously.

In this embodiment, the lever 24 is connected to the linkage assembly 54 at the intermediate portion 50 of the lever 24. The lever 24 when lowered from the elevated position, imparts a downward force on the linkage assembly 54. Thereafter, the linkage assembly 54 fixed at one end by the interior pin 58 rotates about the interior pin and moves the lever 24 in an axial manner. This moves and advances a linkage (not shown) for clamping the tissue. Still further, the member or another component may actuate a timer (not shown) or display to alert the physician/operator to activate the trigger and to initiate the drive source 30. In still another embodiment of the present disclosure, the clamping may be mechanically connected or linked to the drive source 30 to provide for a powered compression of tissue. In still another embodiment, the clamping can be performed simultaneously with the firing of the trigger handle 26, and may be powered by the drive source 30 as opposed to independently of firing.

Once the actuation of the drive source 30 occurs, the drive source will turn the drive gear 74. The drive gear 74 will then directly rotate the second translation gear 76 and the drive screw 66 disposed directly through the bore of the second translation gear. Again, the drive screw 66 will then impart the required axial force to discharge the staples from the staple cartridge 21 in the distal location of the surgical stapler 10. As mentioned, once the drive screw 66 travels a predetermined distance, the drive screw 66 will actuate the corresponding stapler mechanism to fire the staples in the staple cartridge 21.

Figure 7:
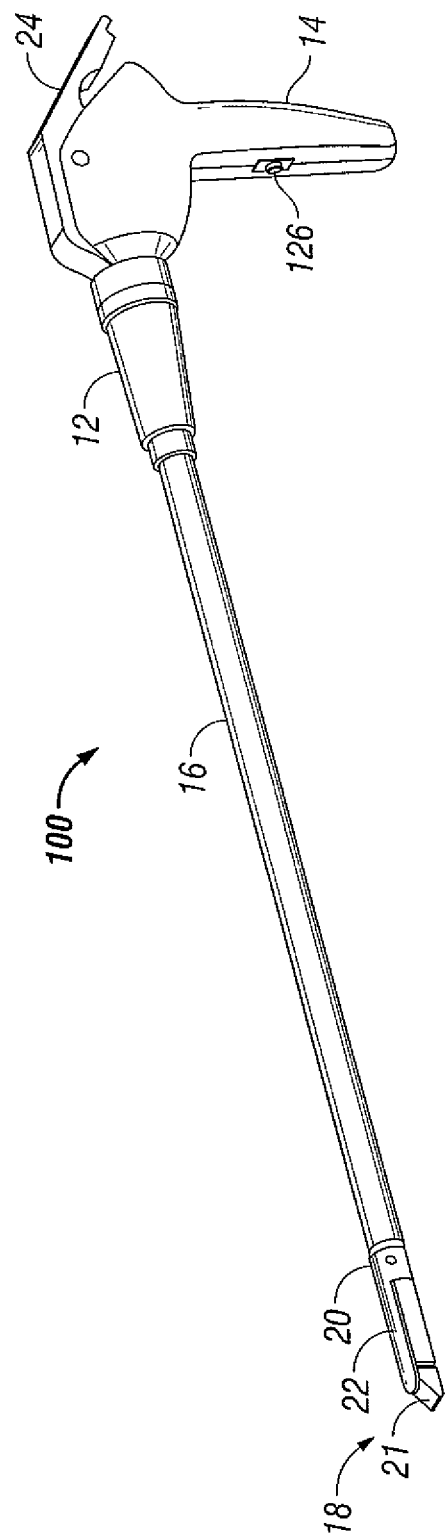
FIG. 7 is a perspective view of a further embodiment of a surgical stapler of the present disclosure.

Referring now to FIG. 7, a self-contained powered surgical stapler constructed in accordance with an embodiment of the subject disclosure is shown and designated generally by reference numeral 100. The surgical stapler 100 is generally intended to be disposable, however the disposable arrangement is non-limiting and other non-disposable arrangements may be contemplated and are within the scope of the present disclosure.

The surgical stapler 100 of the present disclosure (shown in a perspective view in FIG. 7 and described herein) includes a frame generally represented by reference numeral 12 and handle generally represented by reference numeral 14. The frame 12 defines a series of internal chambers or spaces for supporting various inter-cooperating mechanical components of the surgical stapler 100 as well as a number of staples therein for the application to the body tissue.

The frame 12 supports a portion 16 or an extended tube-like portion. The portion 16 is capable of being rotated and has a relatively narrow diameter in a range of about 10 millimeters, and is for insertion into a small opening or tube inserted into the body, such as in the abdominal cavity, or other similar body cavities. The portion 16 has a longitudinal axis and has a length appropriate for reaching the operation site in the interior of the body. The surgical stapler 100 may be used in conjunction with other instruments such as endoscopes or other such optical devices for visually examining the interior of the body, for example, cameras by means of CCD devices, fiber optics or other optical or recording devices.

Generally, portion 16 of the surgical stapler 100 is inserted through the small opening or wound, and is manipulated to the operation site. The present disclosure is intended to be used with any surgical stapler including but not limited to surgical staplers having simultaneous clamping and independent clamping.

Portion 16 has a fastening assembly generally represented by reference number 18 and cutting assembly (not shown) that is known in the art. The fastening assembly 18 and the cutting assembly (not shown) are located in a housing 20 which carries a fastener and an optional cutter to the operation site. The fastening assembly 18 in this particular embodiment has a jaw or a staple cartridge 21 and a second jaw or anvil 22. The staple cartridge 21 and the anvil 22 may be brought into close cooperative alignment with one another so the jaws 21, 22 form a clamp therebetween. The jaws 21, 22 may be a first and second jaw that open and close or may be another different clamping type structure as is known in the art. The staple cartridge 21 may be located at the distal end of the housing 20, in the jaws 21, 22 themselves or may be located in other locations as described in U.S. Pat. No. 7,044,353 to Mastri, et al. which is herein incorporated by reference in its entirety. The staple cartridge 21 has one or a number of rows of staples. The surgical stapler 100 also has an anvil (not shown) and further may include an optional knife (not shown) as is well known in the art for accomplishing the stapling. It is appreciated that the closing of the jaws 21, 22 with the staple cartridge 21 and the anvil 22 may be accomplished by pivoting the anvil 22 relative to the staple cartridge 21, or by pivoting the staple cartridge 21 relative to the anvil 22, or by pivoting both the staple cartridge 21 and the anvil 22 relative to one another.

Generally, actuating the operating portion of the fastening assembly 18 is accomplished via intermediate components disposed on or within the narrow longitudinally extending tubular portion 16. In one non-limiting embodiment, a cylindrical tubular sleeve member surrounds the portion 16. The sleeve may be manipulated in a direction with the longitudinal axis of the surgical stapling device. The sleeve slides onto the anvil 22 for closing the jaws 21, 22 that are biased open by a biasing device (not shown) to accomplish the clamping. The surgical stapler 100 of the present disclosure has three basic actions or functions, however, the present disclosure is intended to be used with any surgical stapler including but not limited to surgical staplers having simultaneous clamping (i.e., clamping and firing the stapler at the same time) and dependent or independent clamping (i.e., clamping prior to the staple firing).

First, portion 16 is introduced into the human or animal body and is positioned with the jaws 21, 22 aligned at the desired stapling site to receive the target tissue. This may involve rotation of the portion 16 relative to the body, either by rotating the surgical stapler 100 as a whole, by rotating simply the portion 16 relative to the frame 12 as permitted, or a combination of both actions. Thereafter (i.e., secondly), the surgical stapler 100 secures the target body tissue between the staple cartridge or jaw 21 in the distal portion of the housing 20 and the anvil 22. This is accomplished by a clamping action of the jaws 21, 22 or alternatively by another similar or different clamping member.

The jaws 21, 22 are allowed to remain in the closed position for a desired period of time depending on the particular tissue. By configuring the jaws 21, 22 to remain closed for a predetermined period of time allows any excess liquid or fluid in the tissues to drain out of the body tissues prior to actuation of the stapling cartridge 21. This ensures that the liquid does not traverse out of the tissues after firing to form non-uniform staples and instead ensures a proper and uniform staple formation.

With the target tissue clamped between the anvil 22 and the staple cartridge 21, a camming surface which surrounds the housing 20 and anvil 22 is employed to close the jaws 21, 22 of the surgical stapler 10 and clamp the tissue between the anvil 22 and the tissue contacting surface of the staple cartridge 21. The jaws 21, 22 are clamped by actuation of a lever 24 opposite the jaws 21, 22 as is known in the art. Thereafter, the surgeon applies the staples to the body tissue. A longitudinally extending channel is employed to deliver longitudinal motion to an axial drive member and a tissue cutting knife as is known in the art.

The axial drive member or an axial drive screw contacts pusher elements. The pusher elements drive the staples through the body tissue against the fastener or forming surface of the anvil as discussed herein. Typically, in the art the surgical stapler 100 fires usually by an actuation of a first trigger handle or alternatively using a trigger switch 126. Thereafter, the clamping action of the jaws 21, 22 is released and the surgical stapler 100 or a portion thereof may be withdrawn from the body.

Figure 8:
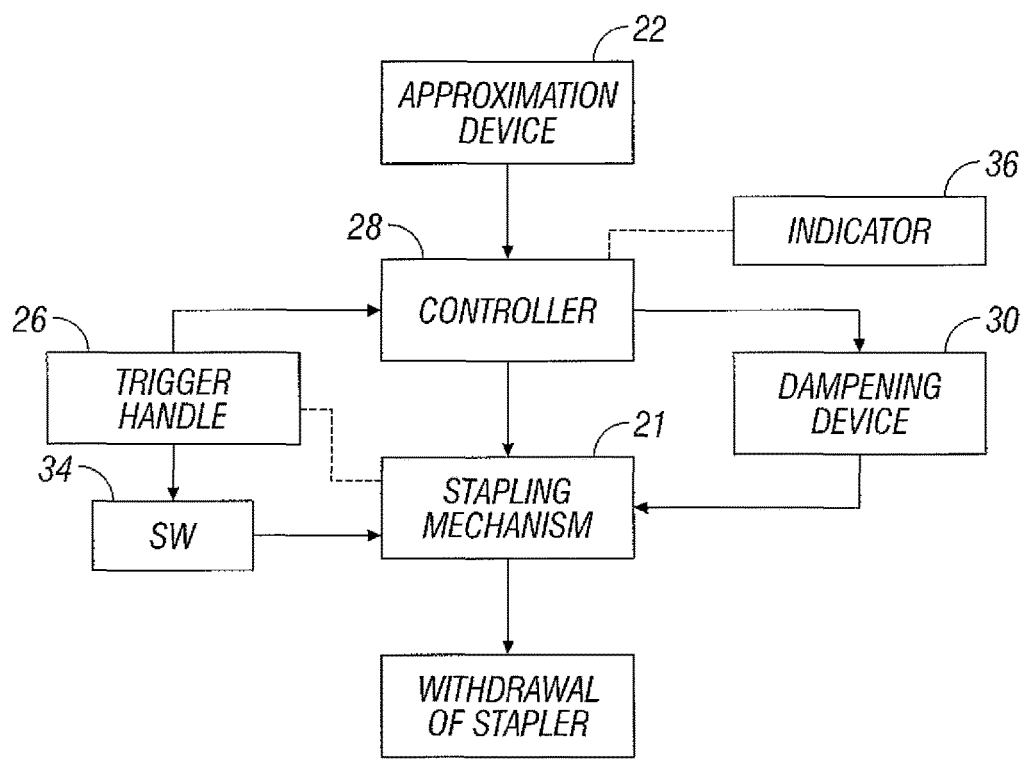
FIG. 8 is a block diagram of a number of components of the surgical stapler of FIG. 7.

Referring now to FIG. 8, there is shown a block diagram of the surgical stapler 100 of the present disclosure. According to a first aspect of the present disclosure, the surgical stapler 100 may have an optional controller 128. The controller 128 is any electronic device being coupled to a memory for executing one or more readable program instructions or alternatively may be a suitable analog circuit. Still further, the controller 128 may be a suitable mechanical member or linkage for controlling one or more functions of the surgical stapler 100.

The controller 128 is connected to an internal or external power supply and a motor and is connected between the anvil 22 and the stapling cartridge 21. In an alternative embodiment, a trigger handle or another actuating switch or component 126 is mechanically or electronically linked or otherwise connected to the stapling cartridge 21 as is known in the art as indicated by a dotted line, and the present disclosure is not intended to be limited to any configuration. Once the stapling cartridge 21 is fired using the trigger switch 126, the jaws 21, 22 are opened and the firing mechanism is retracted. The surgical stapler 100 as a whole may be withdrawn from the body tissue or may be manipulated for a next or second stapling operation as shown.

The present surgical stapler 100 has the controller 128 which is connected to one of the jaw or anvil 21 or jaw or staple cartridge 21 and the trigger switch 126 or is connected to both jaws 21, 22 and the trigger switch 126. In one embodiment, once the desired site is reached, the surgeon uses the jaws 21, 22 to compress the selected body tissue. Alternatively, the surgical stapler 100 may have a single drive component that can actuate both the anvil 22 and stapling cartridge 21.

Thereafter, the controller 28 may provide for a requisite amount of delay between clamping and firing (or after clamping and before firing) to ensure tissue compression and expulsion of fluid before the stapling cartridge 21 is actuated. After the desired compression is reached, the stapling cartridge 21 may be automatically engaged by the controller 128 to fire the staples from the stapling cartridge 21 into the body tissue or alternatively the controller 128 may send a signal to the surgeon thereby informing the surgeon a suggestion that the surgeon is to fire the staples. It is envisioned that the firing may be automatic or manual.

Furthermore, the controller 128 may control the speed with which the staples are fired from the staple cartridge 21. Still further, the controller 128 may control an amount of delay before firing. The controller 128 in one embodiment may provide for a predetermined amount of time to elapse prior to outputting a signal to the stapling cartridge 21. In another powered stapler embodiment, the controller 128 may slow a motor speed to increase the body tissue compression time.

In still another embodiment, the controller 128 may engage a dampening device 130. The dampening device 130 is configured to slow the actuating of the staple cartridge 21 in order to increase the overall compression time of the body tissue. Such a dampening device 130 may be a hydraulic or a pneumatic type damper or any other device that may dampen or modulate the operation of one or more components of the surgical stapler 100. In another embodiment, the trigger 126 may simply hold the fire signal for a predetermined time period in associated control circuitry and upon the expiration of the predetermined time period may communicate the signal to the stapling cartridge 21.

The controller 128 may be configured to slow a motor speed, modulate a gear or, still further, engage a circuitry of the motor to slow an operation thereof to otherwise reduce actuation, i.e., a rotation rate of the axial drive screw. Still further, the surgical stapler 100 may also include an override switch 132. The override switch 132 is an automatic or manual device (or other switch) that selectively disengages the controller 128 to permit direct actuation of the stapling cartridge 21 by the trigger switch 126 without any delay at the surgeon's discretion.

Figure 9A:
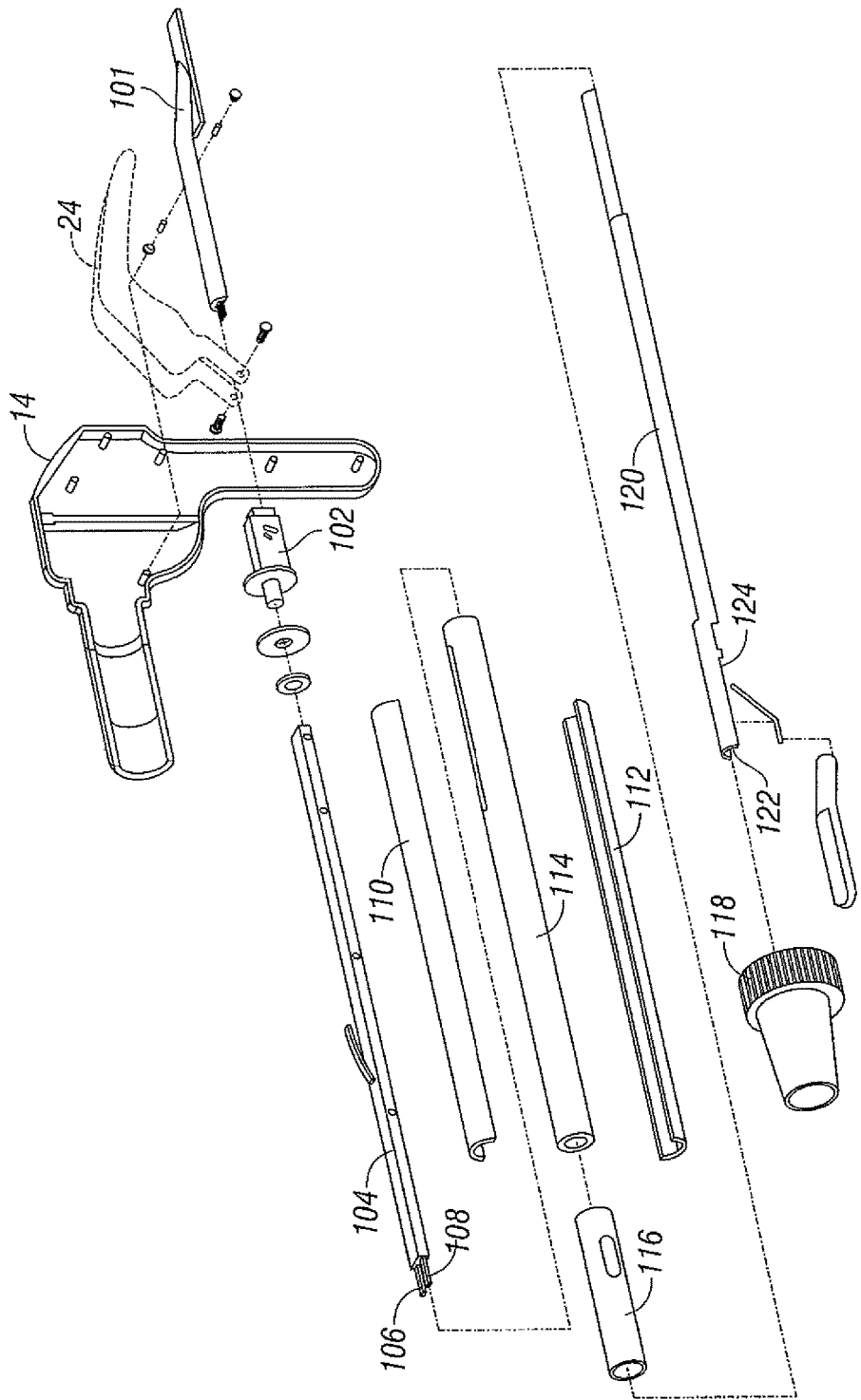
FIG. 9A is an exploded view of a channel of the surgical stapler of FIG. 7.
Figure 9B:
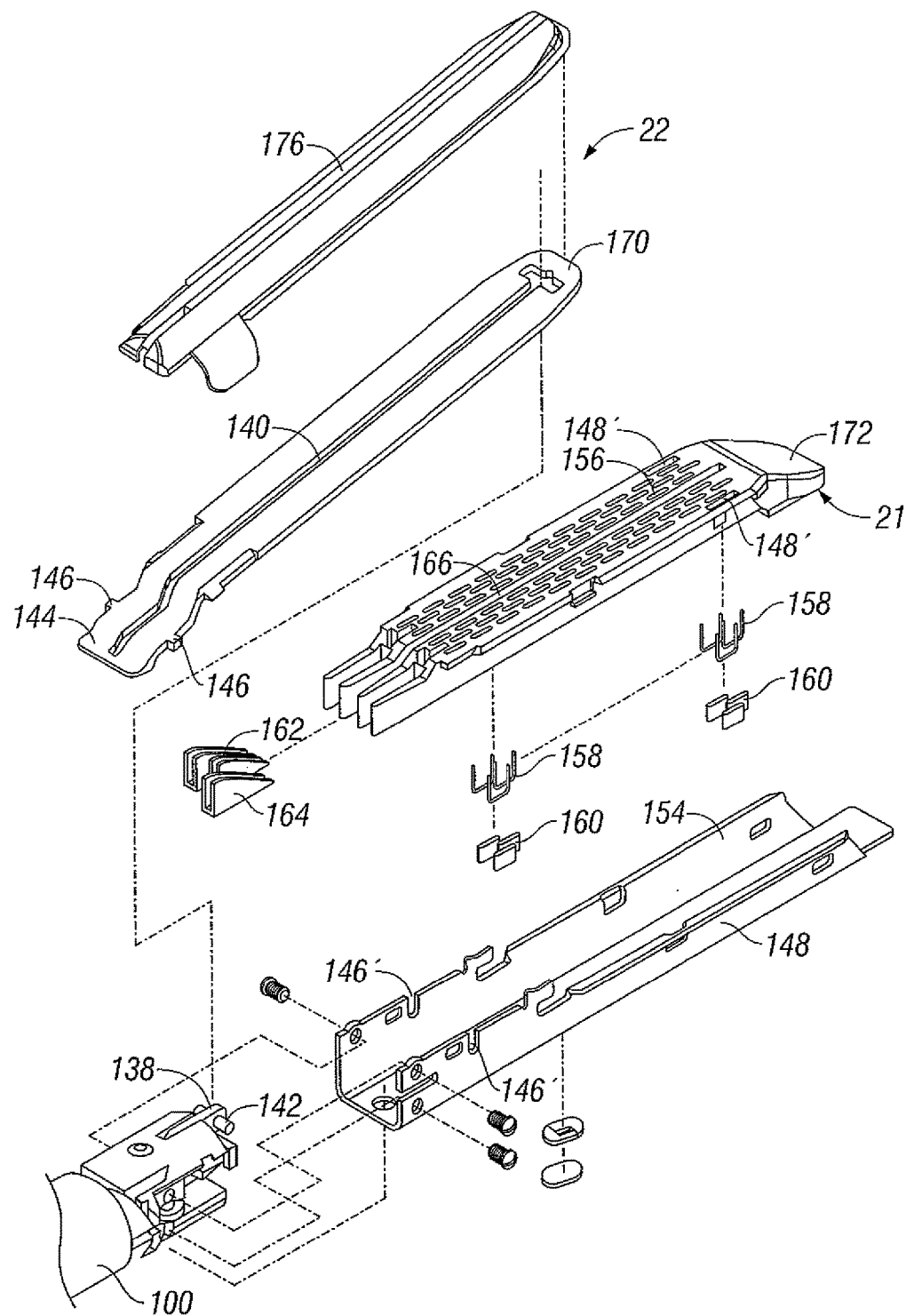
FIG. 9B is an exploded view of the staple cartridge, anvil and the drive sled of FIG. 7.

In one aspect of the present disclosure, the present surgical stapler 100 includes jaws 21, 22 which compresses tissue between the anvil 170 and the stapler cartridge 172 of the stapling cartridge 21 (FIG. 9B). The jaws 21, 22 are understood in the art as a device that allows the surgeon to manipulate and compress tissue between the anvil 170 and the staple cartridge 172 prior to urging of the staples 158 from the staple cartridge 172 as shown in FIG. 9B. The jaws 21, 22 may be independently powered by a power source such as a motor or pneumatic device, or may be powered by the same power source as the staple cartridge 21. The surgical stapler 100 uses the jaws 21, 22 to clamp tissue between the stapler cartridge 172 and the anvil 170 (FIG. 9B), then when the stapler 100 is fired the jaws 21, 22 may be further tightened and then the staples 158 urged from the stapling cartridge 21.

In one aspect, the surgical stapler 100 may pre-clamp or compress tissue using the jaws 21, 22 for a first interval. The first time interval may be preset and fixed, or variable depending on the tissue type. The first time interval may be for minutes, seconds or any other variable or fixed predetermined period of time. Then prior to stapling, the jaws 21, 22 may further tighten to further compress the tissue for another second compression time interval and then fire. The second time interval may be different from the first time interval and can be shorter or longer than the first. In another aspect, the instrument may pre-clamp or compress tissue using the jaws 21, 22 and then simply automatically fire the device to urge the staples 158 from the staple cartridge 132 at the conclusion of the first interval. Various configurations are possible, and the present surgical stapler 100 may have program instructions for any number of compression intervals desired by the surgeon and/or designer. The surgical stapler 100 may alternatively further use a second separate clamping device in association with the stapler 100. It is understood that the present disclosure may be incorporated into an instrument that approximates the tissue before firing such as with a TA surgical stapler such as U.S. Pat. No. 6,817,508 to Racenet, et al. which is herein incorporated by reference in its entirety, or can be used with an instrument that requires no such approximation before firing.

In another embodiment of the present disclosure, the surgical stapling device 100 may provide the surgeon with feedback by virtue of an indicator 136. The indicator 136 may display an amount of compression time and/or provide feedback of the status of the stapling, or display information relating to the location of the drive screw, or drive member. In another embodiment of the present disclosure, the surgical stapler 100 may not have separate clamping and firing actuators and include a clamping gradient indicator 136 or simultaneous clamping and firing indication mechanism. For example, the surgical stapler 100 may be configured to allow control of the firing speed which, in turn, controls the clamping speed and timing and then provide optimal compression for squeezing the tissue and pushing the blood and fluid out of the tissue at the desired site.

FIG. 9A shows an exploded view of a number of components of the surgical stapler 100 of FIG. 7. The stapler 100 has a rack 101 that is slidable in the handle portion 14. The rack 101 interfaces with a clamp tube 102. On a distal side of the clamp tube 102 is a channel 104. The channel 104 engages with the clamp tube 102 and a pair of forks 106, 108 on a distal side thereof. The stapler 100 also has an upper cover 110 and a lower cover 112, and an extension tube 114. The extension tube 114 engages with a collar tube 116. The stapler 100 also has a rotation knob 118 with a channel portion 120. The channel portion 120 has a pair of camming surfaces 122 on a distal end. The distal end also has a crimp 124 in a distal side to receive the anvil portion 170 of jaw 22.

In operation, the rack 101 slides and moves the clamp tube 102 distally. The clamp tube 102 is provided to interconnect the handle portion 14 and the extension tube 114. The channel 104 is slidably mounted for reciprocal longitudinal motion. The extension tube 114 provides support for the surgical stapler 100 and has slots that interface with the collar tube 116. The surgical stapler 100 also has a support 120 for longitudinal motion and to operate the stapling mechanism as described in FIG. 9B. The operation of these components is well known and is disclosed in U.S. Pat. No. 5,318,221 to Green, et al., which is herein incorporated by reference in its entirety.

Advantageously, the rack 101 moves distally to advance the channel 104 in a distal manner. The channel 104 delivers longitudinal motion to a pusher cam bar as is known in the art for operation of stapler cartridge 172 of jaw 21 shown in FIG. 9B. It should be appreciated that the components shown in FIG. 9A only illustrate one embodiment of the present surgical stapler 100, and instead of the rack 101, the surgical stapler 100 may have a drive screw (not shown) for longitudinal motion and in order to actuate the stapler cartridge 172.

Referring now to FIG. 9B, there is shown an exploded view of the jaw 22 having an anvil portion 170 and the jaw 21 having a stapler cartridge 172 including an actuation sled 169. The anvil portion 170 of jaw 22 includes a plurality of staple deforming concavities (not shown) and a cover plate 176 secured to a top surface of anvil portion 170 to define a cavity (not shown). The cover plate 176 prevents pinching of tissue during clamping and firing of the surgical stapler 100. The cavity is dimensioned to receive a distal end of an axial drive assembly 138.

The anvil portion 170 has a longitudinal slot 140 that extends through anvil portion 170 to facilitate passage of retention flange 142 of the axial drive assembly 138 into the anvil slot 140. A camming surface 144 formed on anvil portion 170 is positioned to engage axial drive assembly 138 to facilitate clamping of tissue. A pair of pivot members 146 formed on anvil portion 170 is positioned within slots 146' formed in carrier 148 to guide the anvil portion 170 between the open and clamped positions.

The stapler 100 has a pair of stabilizing members 152 engage a respective shoulder formed on carrier 148 to prevent anvil portion 170 from sliding axially relative to staple cartridge 172 as camming surface of the anvil portion 170 is deformed. Cartridge assembly 172 includes the carrier 148 which defines an elongated support channel 154. Elongated support channel 154 is dimensioned and configured to receive the staple cartridge 172 which is shown above the carrier 148 in the exploded view of FIG. 9B. Corresponding tabs and slots formed along staple cartridge 172 and elongated support channel 148' function to retain staple cartridge 172 within support channel 154 of carrier 148. A pair of support struts formed on the staple cartridge 172 are positioned to rest on side walls of carrier 148 to further stabilize staple cartridge 172 within support channel 154, however other arrangements to support the cartridge 172 on the channel 154 can be used and this arrangement is not limiting.

Staple cartridge 172 includes retention slots 156 for receiving a plurality of fasteners 158 and pushers 160. Longitudinal slots 156 extend through staple cartridge 172 to accommodate upstanding cam wedges 162 of the actuation sled 164. A central longitudinal slot 166 extends along the length of staple cartridge 172 to facilitate passage of a knife blade (not shown). During operation of surgical stapler 100, actuation sled 164 is drive distally to translate through longitudinal slot 156 of staple cartridge 172 and to advance cam wedges 162 distally and into sequential contact with pushers 160, to cause pushers 160 to translate vertically within slots 156 and urge fasteners 158 from slots 156 into the staple deforming cavities of anvil assembly portion 170 to effect the stapling of tissue.

Figure 10:
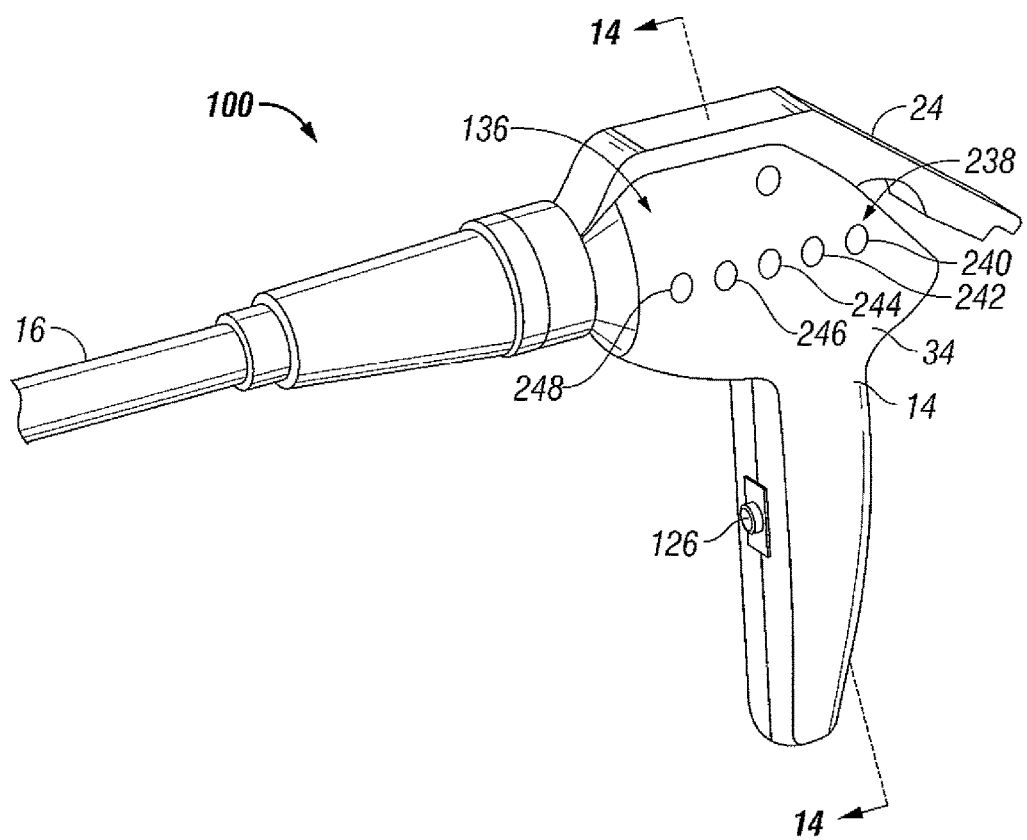
FIG. 10 is a perspective view of another embodiment of a surgical stapler of the present disclosure having a number of lights.

Referring to FIG. 10, the surgical stapler 100 may include indicator 136 which may be any device known in the art to provide sensory feedback to the surgeon. The indicator 136 may be any device that permits a visual, tactile or audible monitoring of one or more conditions of the surgical stapler 100. The indicator 136 may be disposed on outer surface 34 and/or disposed on the handle 14. Alternatively, the indicator 136 may be disposed on portion 16 of surgical stapler 100, on the trigger switch 126, on the lever 24 or in any other suitable location where the indicator 136 may be easily viewed by the surgeon without a change in position or change in footing by the surgeon.

In one embodiment, as shown the indicator 136 includes a number of light bulbs 238. The lights 238 may be one light or a series of many lights bulbs or LEDs with one color or an assortment of two or more colors. Each of the lights 238 may have a color representing one or more conditions of the surgical stapler 100. Alternatively, one or all of the lights 136 may flash to indicate a condition of the surgical stapler 100.

Upon being actuated by the trigger switch 126, the surgical stapler 100 may impart a delay before firing of the staples. However, in order to provide the proper feedback to the surgeon, the lights 238 provide, for example, a visual indication of the progress of the firing of the stapling cartridge 172. For example, still referring to FIG. 10, there is shown a first light 240, a second light 242, a third light 244, a fourth light 246, and a fifth light 248. As the axial drive screw (not shown and in the handle) travels the predetermined drive path the lights 240, 242, 244, 246, and 248 illuminate in series to portray the relative distance of the drive screw on the exterior of the handle. When the lights 240, 242, 244, 246, and 248 are illuminated, the stapling cartridge 172 fires which ensures that proper tissue compression occurs prior to deployment of the staples.

Figure 11:
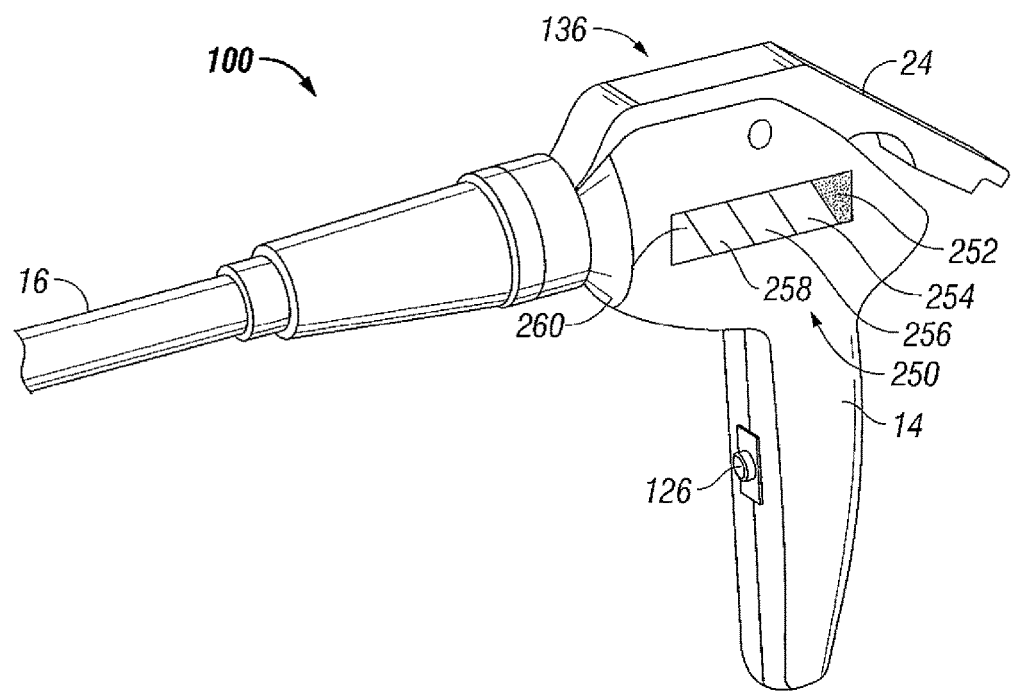
FIG. 11 is a perspective view of still another embodiment of a surgical stapler with a linear display.

Referring now to FIG. 11, in another exemplary embodiment of the present disclosure, the surgical stapler 100 includes a linear indicator 250 having a plurality of discrete segments, first segment 252, second segment 254, third segment 256, fourth segment 258, and fifth segment 260. Again, once the trigger switch 126 is actuated to fire the stapling cartridge 172, the segments 252, 254, 256, 258, and 260 each illuminate in a predetermined pattern to indicate to the surgeon the status of the progression of the drive screw in the handle 14.

Upon all of the segments 252, 254, 256, 258, and 260 being illuminated, the stapling cartridge 172 fires the staple into the body tissue with assurance that an amount of compression time of the body tissue has lapsed. Linear display 250 may have one or more different colors or combinations of colors to indicate a position of the drive screw such as "red" to indicate firing and "green" to indicate that the firing is complete or vice versa. Still further the linear display 250 may display one or more graphical representations, images, or pictures to indicate one or more conditions or operating parameters of the surgical stapler 100.

For example, the linear display 250 may indicate "FIRE" or "COMPLETE", or any other graphical representation to indicate that surgical stapler 100 will fire at the predetermined time period. Various possible combinations are possible and all are within the scope of the present disclosure.

Figure 12:
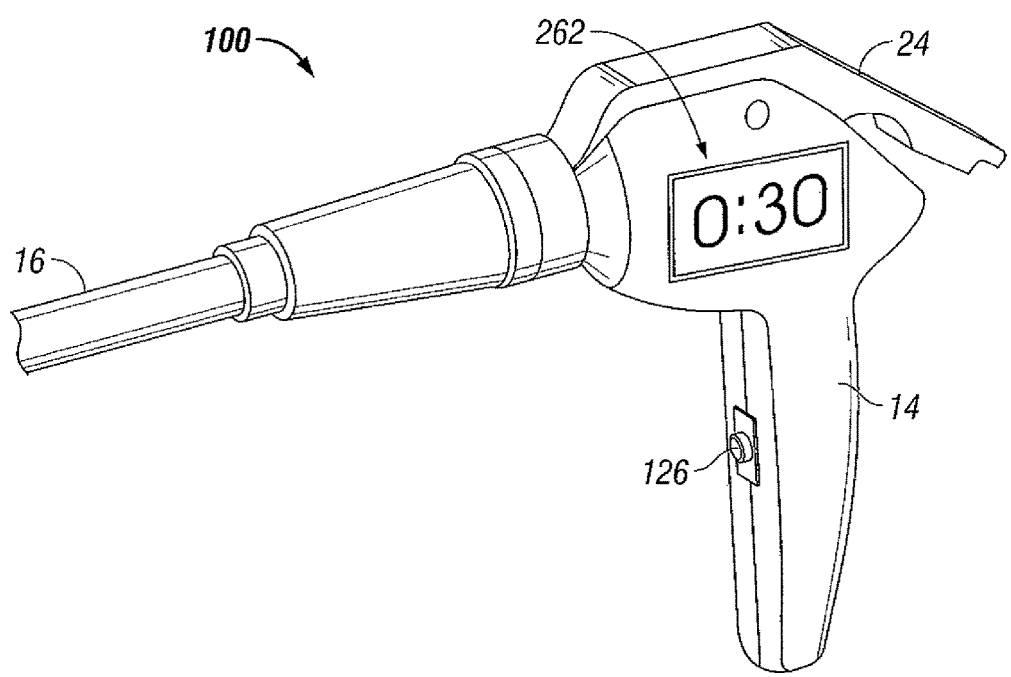
FIG. 12 is a perspective view of yet another embodiment of a surgical stapler having a digital display.

In still another exemplary embodiment of the present disclosure shown in FIG. 12, the surgical stapler 100 may include a digital display 262. The digital display 262 may indicate a count down or count up (or other time interval) after actuation of the trigger switch 126. For example, the digital display 262 may count down to the desired stapling time after compression to ensure a predetermined amount of tissue compression by the jaws 21, 22. The digital display 262 may be activated by the jaws 21, 22 being brought in close alignment with one another or activated independent of clamping. A desired clamping interval may be preset for desired tissue.

Alternatively, the digital display 262 may be selectively preset and input by the surgeon using an input device (not shown) or button. The surgeon may input a time period of clamping into the display 262. Thereafter, the display 262 will suggest firing at the elapse of the clamping time period, or may automatically fire after a predetermined clamping time elapses (e.g., such as from about ten seconds to forty five seconds) to ensure proper tissue compression. The digital display 262 may be configured to count down from the predetermined set interval of clamping and visually communicate a signal to the controller 128. The controller 128 after receiving the signal allows the desired time period of clamping to elapse. After the set time period expires, the controller 128 may communicate a second signal to actuate the stapling cartridge 172. Alternatively, the controller 128 may simply modulate the speed of the motor to commence operation at a speed suitable to actuate the stapling cartridge 172 at the end of the desired time period. In still yet another embodiment, the digital display 262 may be configured to initiate counting after commencement of the clamping of tissue and then simply display the time from that point onwards to allow the surgeon to monitor and manually actuate the trigger switch 126 at the expiration of the desired time period. Thereafter, the digital display 262 may simply display or flash the compression time to the surgeon and the exact amount of elapsed time. It is appreciated that the instrument may provide a predetermined delay and then indicate that the instrument is ready to be manually fired, or alternatively the instrument may delay then indicate and then automatically fire.

Figure 13:
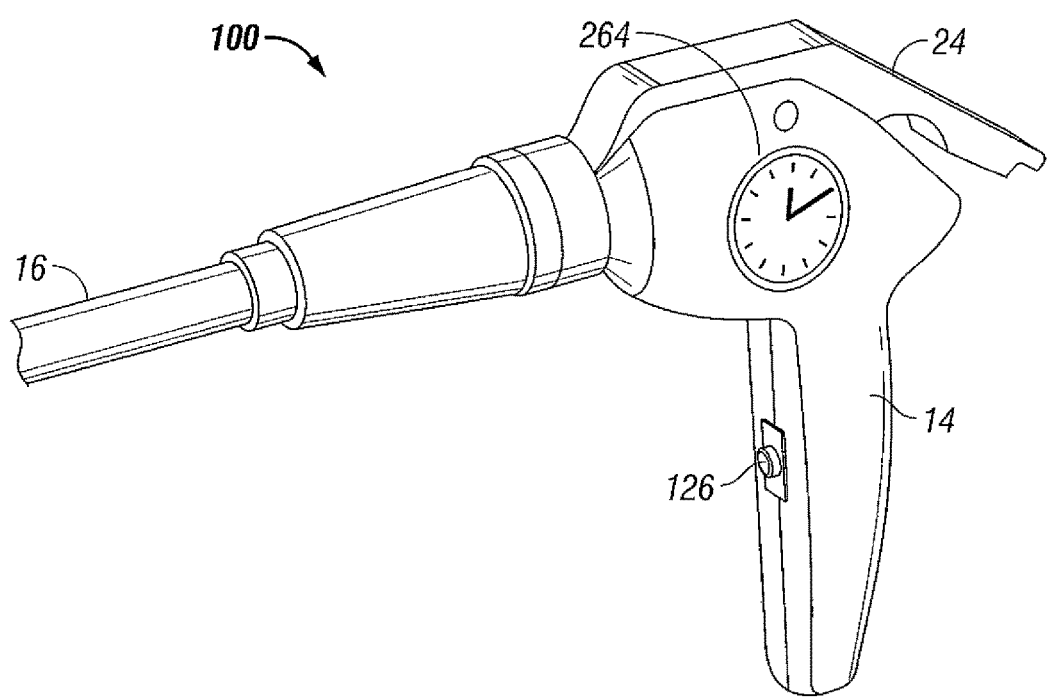
FIG. 13 is a perspective view of still another embodiment of a surgical stapler with an analog display.

Referring now to FIG. 13, the surgical stapler 100 may alternatively have an analog display 264 disposed on the outer surface of the handle 14 which functions similar to the digital display 262. Analog display 264 may have an audible alarm or alternatively have a flashing light to indicate that the appropriate tissue compression time has been reached or exceeded.

Figure 14:
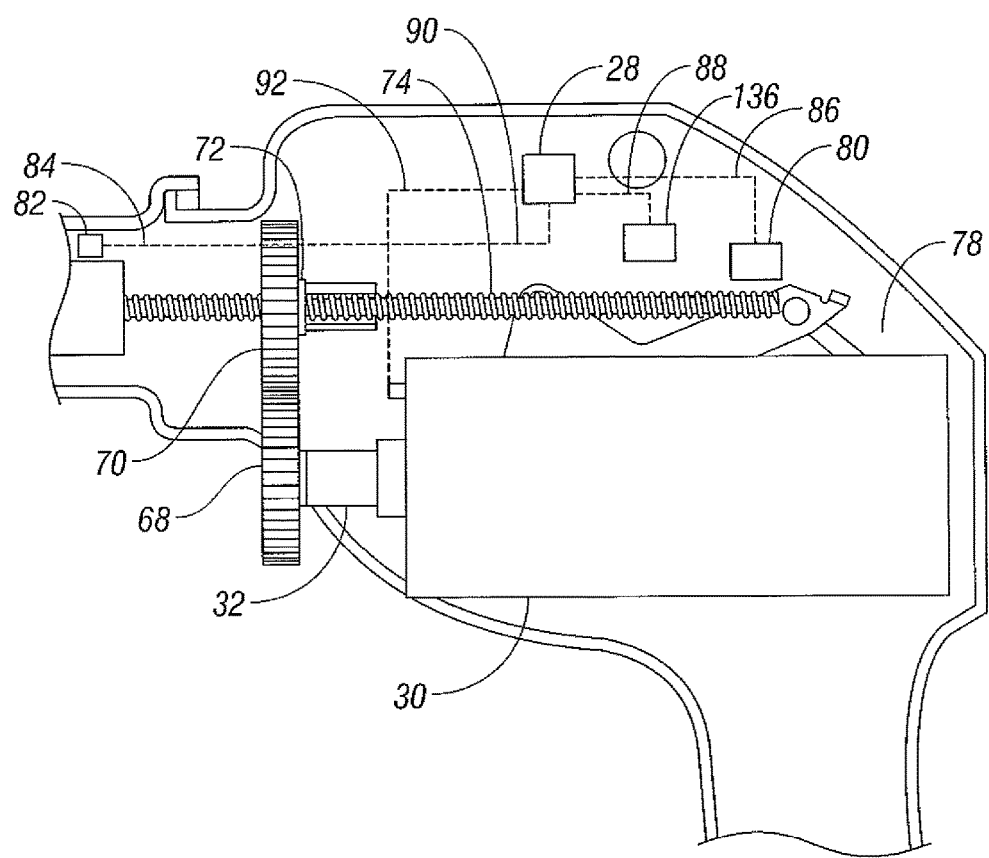
FIG. 14 is a cross sectional view of the surgical stapler along line 14-14 of FIG. 10.

Referring now to FIG. 14, there is shown a cross sectional view of the handle 12 of the surgical stapler along line 14-14 of FIG. 10. In this embodiment, the surgical stapler 100 is a powered device and has a motor 30 with a driving mechanism. The driving mechanism is a drive output shaft 32. Shaft 32 connects to a first gear 68. The first gear 68 is connected to a second gear 70 which, in turn, engages an axial drive screw 74. The motor 30 may be a device that drives one or more components of the surgical stapler 100.

The drive screw 74 is a threaded rod having a number of helical grooves that are intended to rotate and contact another member to actuate the stapling cartridge 172 in the distal location of the surgical stapler 100 once compression is made by the surgeon using the clamp or jaws 21, 22. The axial drive screw 74 is disposed in toothed engagement through a central bore 72 of the second gear 70. The axial drive screw may also be disposed offset from the second gear 70 or in any other desired geared arrangement. Upon actuation of the motor 30, the axial drive screw 74 rotates and traverses distally through the portion 16 of the surgical stapler 100 to engage the stapler cartridge 172 as is well known in the art. Alternatively, the surgical stapler 100 may have a drive piston or plunger instead of the axial drive screw 74 or a single drive mechanism to control both the anvil portion 170 and the stapling cartridge 172. Such mechanisms are well known in the art and may be found in U.S. Pat. No. 6,330,965 B1 to Milliman, et al., U.S. Pat. No. 6,250,532 B1 to Green, et al., U.S. Pat. No. 6,241,139 B1 to Milliman, et al., U.S. Pat. No. 6,109,500 to Alli et al., U.S. Pat. No. 6,202,914 B1 to Geiste, et al., U.S. Pat. No. 6,032,849 to Mastri, et al. and U.S. Pat. No. 5,954,259 to Viola, et al., which are all herein incorporated by reference in their entirety.

The surgical stapler 100 may include a first switch 80. Switch 80 is located in a fixed position of the handle as shown. The stapler 100 also has a second switch 82 disposed distally relative to the first switch 80 that is distal or near the path of the drive screw 74 in the first initial position 78. Likewise, the second switch 82 in a second firing position 84 which is disposed distally from the first initial position and proximal or near the path of the drive screw 74. Each of the first and second switches 80, 82 is a limit switch, but alternatively may be any switch known in the art to change or toggle from a first position to a second position by a simple motion of the axial drive screw 74 traversing past or adjacent to the respective limit switch.

Once the axial drive screw 74 or a portion thereof traverses past the first switch 80, the first switch communicates a signal to the controller 128 by lead 86. The controller 128 thus illuminates the indicator 136 or a portion thereof by lead 88 to indicate to the surgeon a first location of the axial drive screw 74.

Thereafter, the drive screw 74 or a portion thereof traverses or contacts the second switch 82 at the second firing position 84. The second switch 82 is also a limit switch and communicates a second signal to the controller 128 by lead 90 of the location or firing of the stapler cartridge 172. The controller 128 then illuminates indicator 136 (or another portion thereof) by lead 88 to indicate to the surgeon that the stapling has been completed. At the conclusion of the stapling, the surgeon/operator will initiate retraction and then will reverse a direction of the motor 30 by lead 92. The motor 30 then reverses operation and returns the axial drive screw 74 to the initial position 78 for the next stapling operation.

Alternatively, controller 128 upon receiving the first signal from the first switch 80 by lead 86 modulates one or more operations of the surgical stapler 100. For example, in response to receiving of the first signal, the controller 128 can control one or more parameters of the surgical stapler 100 including tissue gap, speed of the motor 30, control stroke of the axial drive screw 74, axial drive screw travel distance, rotational rate of the axial drive screw and any combinations thereof.

Figure 15:
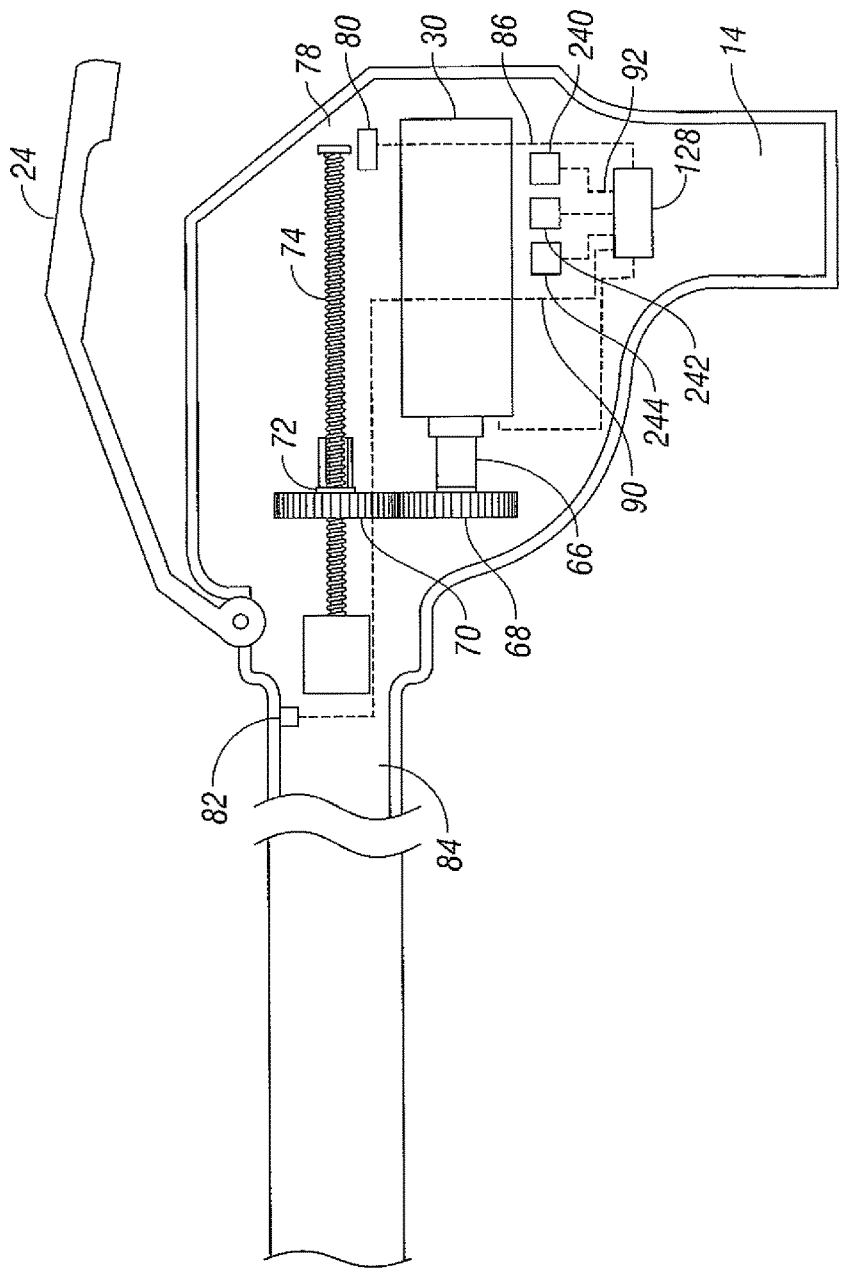
FIG. 15 is another cross sectional view of still another embodiment of a surgical stapler of the present disclosure along line 14-14 of FIG. 10 with the stapler having a first switch and a second switch.

Referring now to FIG. 15, the surgeon may operate/engage the firing mechanism in order to actuate the stapling cartridge 172. The firing mechanism actuates the motor 30 shown in FIG. 15. The axial drive screw 74 commences rotation and by traversing past switch 80 the drive screw 74 actuates the first switch 80. The first switch 80 outputs the signal to the controller 128 by lead 86. The controller 128 in response to the signal from the first switch 80 then actuates the first light 240 by lead 92. The surgical stapler 100 may further have a suitable structure in order to engage a stop feature. The stop feature prohibits overdrive of the drive screw 74.

Thereafter, after the axial drive screw 74 traverses a predetermined distance to ensure tissue compression by the clamp or jaws 21, 22. The second switch 82 is actuated and outputs a second signal to the controller 128 by lead 90. The controller 128 in response to the second signal illuminates the second light 242 by lead 94. The second light 242 indicates that the stapling cartridge 172 has fired. The second switch 82 may further emit a signal to the controller 128 to reverse or cease motion in that direction of the motor 30 or to return the axial drive screw 74 to the initial position. The physician/operator may also manually reverse the direction of the motor 30. A third light 244 may illuminate to indicate to the surgeon that the axial drive screw 74 is returning to the initial position 78.

Figure 15A:
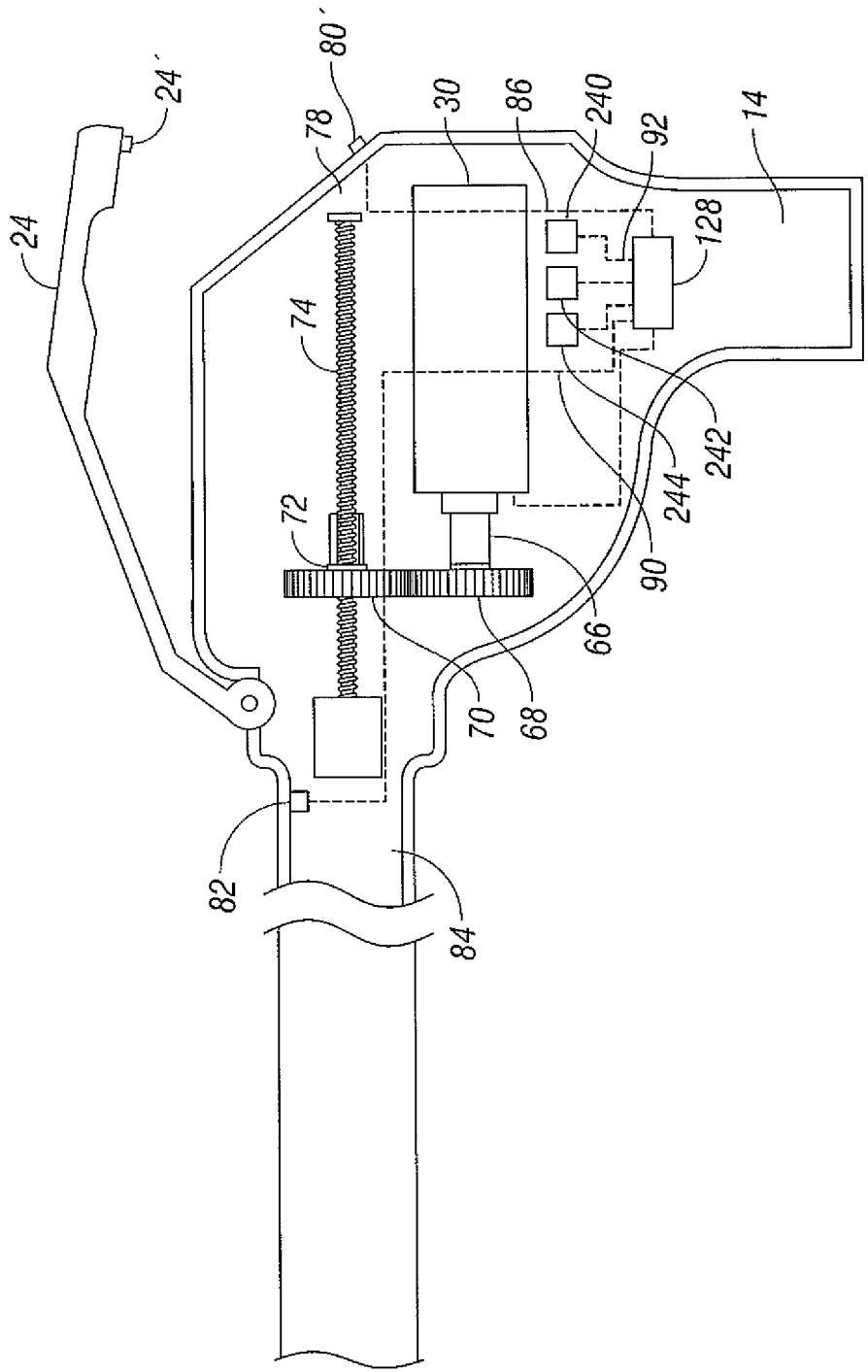
FIG. 15A is another cross sectional view of another embodiment of the stapler of FIG. 15 having the first switch which engages a tab on the lever.

FIG. 15A illustrates another embodiment of the present stapler. In the embodiment shown, the surgeon may operate/engage the firing mechanism in order to actuate the stapling cartridge 172. However, the first switch 80' is in a different location than the embodiment shown in FIG. 15. In this embodiment, the first switch 80' is located immediately under the lever 24 proximal to handle 14. The switch 80' in the embodiment of FIG. 15A engages a tab 24' disposed on the lever 24. When the lever 24 is actuated and driven toward the handle 14, the tab 24' contacts switch 80', and the switch 80' outputs the signal to the controller 128 by lead 86. The controller 128 in response to the signal from the first switch 80 then actuates the first light 240 by lead 92.

Thereafter, after the axial drive screw 74 traverses a predetermined distance to ensure tissue compression by the clamp or jaws 21, 22, the second switch 82 is actuated and outputs a second signal to the controller 128 by lead 90. Again, the controller 128 in response to the second signal illuminates the second light 242 by lead 94. The second light 242 indicates that the stapling cartridge 172 has fired. The second switch 82 that is actuated by switch 80' may further emit a signal to the controller 128 to reverse or cease motion in that direction of the motor 30 or to return the axial drive screw 74 to the initial position. A third indicator 244 may be included to indicate to the surgeon that the axial drive screw 74 is returning to the initial position 78.

Figure 15B:
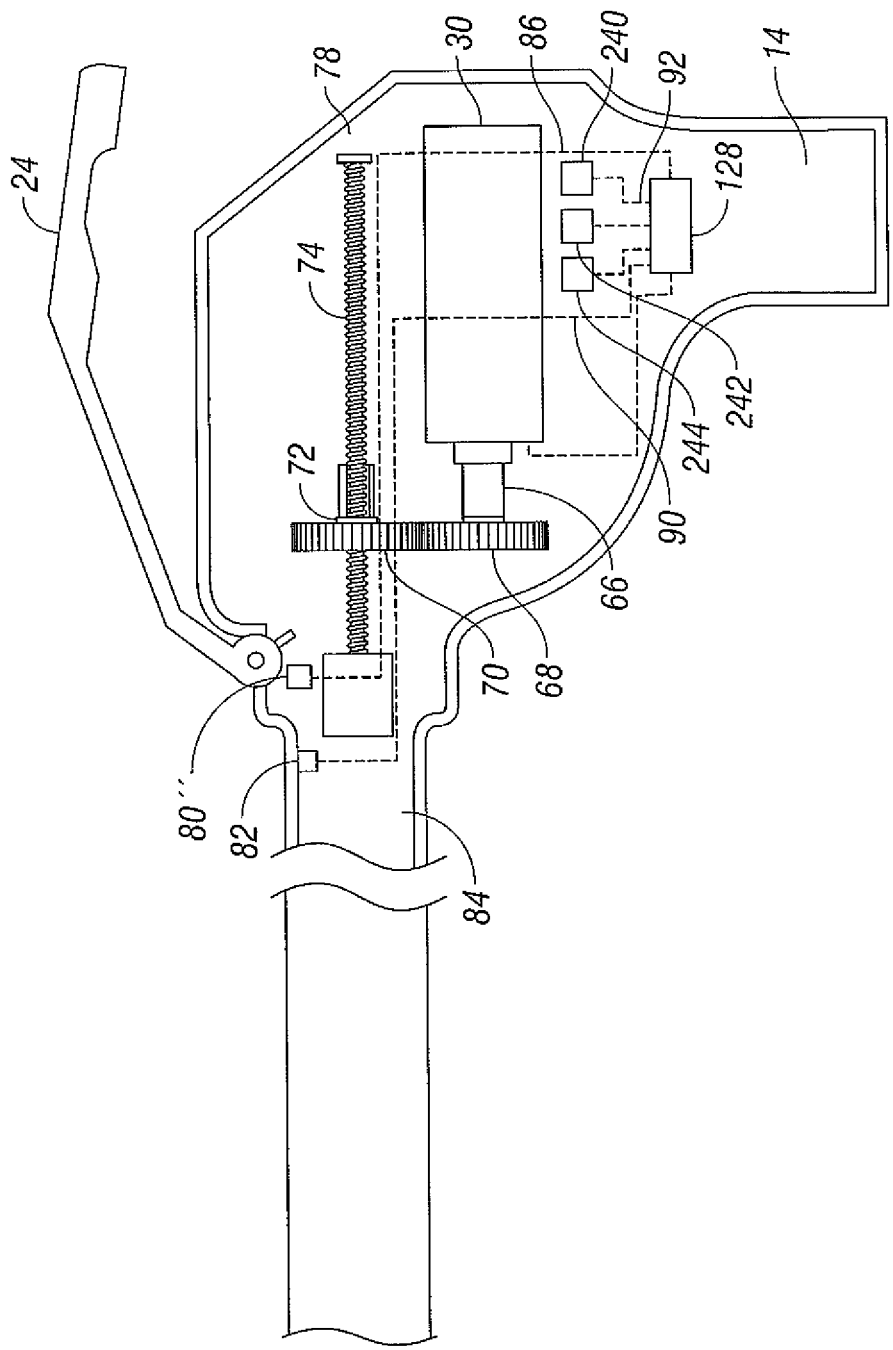
FIG. 15B is still another cross sectional view of yet another embodiment of the stapler of FIG. 15 having the first switch located distally on the lever.

FIG. 15B shows still another embodiment wherein the first switch 80" is located at still another location of the handle 14, and on an opposite distal side of the lever 24 in proximity to pivot. Various configurations are possible and within the scope of the present disclosure, and switch 80" may be placed in various configurations relative to the lever 24.

Figure 16:
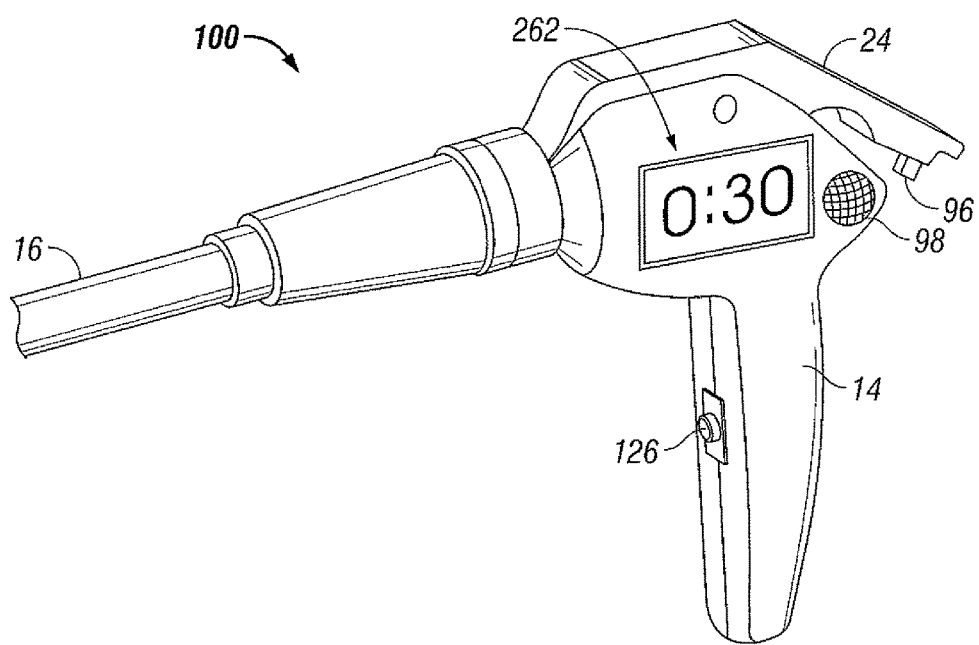
FIG. 16 is another perspective view of still another embodiment of a surgical stapler with an audible alarm.

FIG. 16 shows the surgical stapler 100 with a lever 24. The lever 24, shown in the elevated position, controls the clamp of jaws 21, 22, however this arrangement is not limiting and another driving member may control the clamp of jaws 21, 22 such as the motor 30 (FIG. 14). The lever 24 opens and closes the jaws 21, 22 of the clamp to compress the body tissue prior to surgical stapling. The surgical stapler 100 further includes an electrical contact 96 with an electrically conductive member to complete a suitable analog or digital circuit. The electrical contact 96 is in a complementary nesting location of the lever 24 when the lever is in a lowered position or mating with the handle 14. When the lever 24 is lowered from an elevated or raised position to the lowered position or contacting the handle 14, the lever 24 engages the electrical contact 96. The electrical contact may complete a suitable timer circuit of the display 262 when in the lowered position. In this embodiment, the electrical contact 96 commences the display 262. The display 262 may count upwards from zero to a predetermined time limit, or may count down from an ideal predetermined tissue compression time interval. Once the displayed time reaches the predetermined time interval, an audible alarm 98 may sound. The audible alarm 98 provides the surgeon with a cue that the optimal tissue compression time has been reached, and that the firing mechanism should be actuated in order to fire the staple from the staple cartridge 172 to ensure a uniform staple formation.

Figure 17:
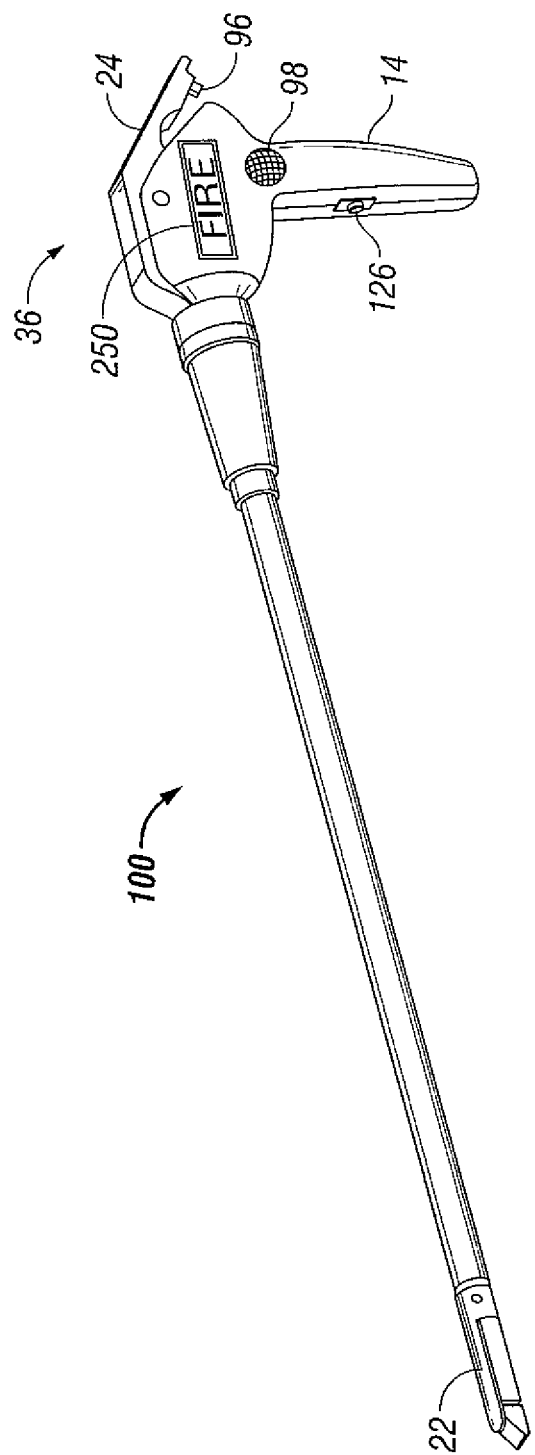
FIG. 17 is still another perspective view of another embodiment of a surgical stapler having the display showing an image.

FIG. 17 illustrates in still another embodiment where the clamp formed by jaws 21, 22 is actuated by lowering the lever 24. Contemporaneously, the timer circuit of the display 262 is activated by the electrical contact 96 on the lever 24. The indicator 36 may be the linear display 250 which indicates a first color to prompt for the actuation of the staple cartridge 172 by the trigger switch or button 126. The display 250 may then display a second image or illuminate the number of segments corresponding to a travel path of the axial drive screw 74 as shown in FIG. 14. Upon actuation, the second switch 82 outputs a signal to the controller 128. The controller 128 then stops the motor 30, and the controller outputs a control signal to the display 250 to modulate the display from the first color to another second color or from a first image to a second image to indicate that the staple cartridge 172 has fired. Optionally, the controller 128 may further sound the audible alarm 98 indicating that the staple cartridge 172 has fired. The alarm may be any sound or audible pattern, including a buzzer, a song, a chirp, a chime or any combinations thereof. Various indicator configurations are possible and within the scope of the present disclosure.

In still another embodiment, the jaws 21, 22 may be actuated by lowering the lever 24. Contemporaneously, the timer circuit of the display 262 is activated by the lever 24. Thereafter, the indicator 136 indicates a first indication to prompt for an actuation of the staple cartridge 172 by actuating switch 126 after a desired time period elapses. Once the trigger switch 126 is actuated, the controller 128 activates the motor 30. The motor 30 then moves the drive screw 74 as shown in FIG. 14.

Figure 18:
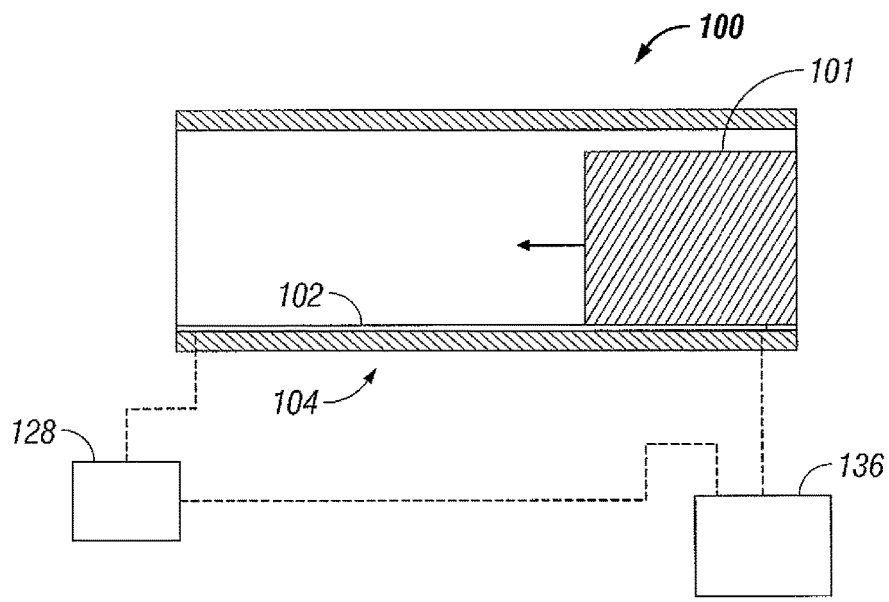
FIG. 18 is a cross sectional view of a travel path of a drive member through an endoscopic portion of a surgical stapler with a resistor strip.

As the axial drive screw 74 moves in an axial manner, the drive screw (or another plunger 101 connected thereto as shown in FIG. 18, contacts a second member 102. Second member 102 may be any member that modulates based on the motion of the plunger 101 and that can be detected or sensed by another device to provide an indication to the surgeon. The second member 102 may be a resistor strip which changes a resistance along a travel surface 104 of the plunger 101 as the plunger 101 or the axial drive screw 74 traverses along the portion 16 of the surgical stapler 100 (or other suitable travel surface location). The resistor strip 102 is coupled to indicator 136 such that the change in resistance of the resistor strip 102 selectively illuminates each of the lights 240 through 248 to signal an amount of travel by the axial drive screw 74 or the plunger 101 or other suitable drive member.

Alternatively, the resistor strip 102 may be coupled to another indicator 136 such as a linear display 250. The display 250 may illuminate the number of segments 252, 254, 256, 258, and 260 corresponding to a travel of the axial drive screw 74 or the plunger 101 until the axial drive screw actuates the staple cartridge 172. Upon actuated, the resistor strip 102 outputs a signal to the controller 128 which modulates the operation of the motor 30, and sends another second signal to the display 250 to indicate that the staple cartridge 172 has fired. The display 250 in response thereto may then display a suitable graphical image, another color, a textual message, or any other indication to indicate to the surgeon that the firing of the staple cartridge 172 has concluded. Various indicator configurations are possible and within the scope of the present disclosure.

Figure 19:
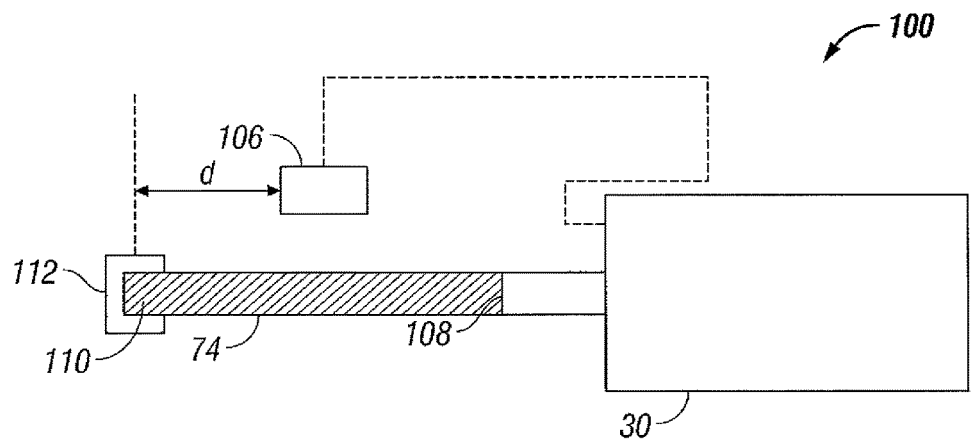
FIG. 19 is a graphical representation of another embodiment of a surgical stapler having a non-contact sensor.

Referring now to FIG. 19, in yet another embodiment of the present disclosure, the surgical stapler 100 may further include a non-contact sensor 106. The non-contact sensor 106 may optionally be a so-called "Hall effect non-contact sensor" (or alternatively any other non-contact sensor) that is based in part on the physical principle of the Hall effect named after its discoverer E. H. Hall.

For example, end 108 of the axial screw 74 is directly connected, geared to, or offset from the motor 30, and a cap like free end 110 of axial screw 74 contacts the staple cartridge 172 to actuate the stapler cartridge and to fire the staple as discussed previously. The free end 110 of the drive screw 74 has a magnetic member 112 which connects thereto and which will not become dislodged by a rotation of the drive screw 74. Alternatively, the magnetic member 112 may be disc shaped and simply connect to the free end 110. In one initial orientation, free end 110 and the magnetic member 112 are disposed closely adjacent, or near to the non-contact sensor 106. At this initial orientation, the magnetic member 112 is separated by a first distance "d" from the non-contact sensor 106.

Once the trigger switch or button 126 is actuated, the motor 30 is actuated, and rotates, the drive axial screw 74 to traverse distally to actuate the staple cartridge 172 as described above. In the second orientation after the motor 30 has been actuated, the magnetic member 112 moves and is a second distance "d" away from the non-contact sensor 106. The second distance is any distance greater than the first distance "d". As the magnetic member 112 moves away from the non-contact sensor 106, the non-contact sensor now located the second distance away from the magnetic field of the magnetic member 112 modulates an operation of the motor 30.

The term "modulation" is defined as modulating amount of voltage received by the motor 30 in a dynamic manner, turning the motor "off" at a desired stroke, changing the motor speed, drive gear reduction of the motor, reduction of the axial drive screw pitch, or a change in the voltage or the current input of the motor, or changing another firing component, a change of the motor components and any combinations thereof. This may thereby slow the operation of the motor 30 to increase an amount of compression time of the body tissues between jaws 21, 22. In another alternative embodiment, the magnetic member 112 may be disposed on a suitable drive piston instead of the drive screw 74. As the drive piston travels away from the non-contact sensor 106, a reduced or modulated amount of voltage may be provided to the motor 30. Still further in another alternative embodiment, the non-contact sensor 106 may be placed at the free end 110 of the drive screw 74 and the magnetic member 112 fixed.

In another embodiment of the present disclosure, the surgical stapler may have a combined drive mechanism. The combined drive mechanism may control both a firing component of the stapling mechanism and a clamping mechanism. The surgical stapler 100 may, upon being actuated, has the drive mechanism advance to commence the clamping using the clamping mechanism and then hold and wait thus providing a predetermined delay. The surgical stapler 100 would then provide an indication to the surgeon/operator once a desired amount of compression is reached. Thereafter, the surgeon/operator would then actuate the drive mechanism after the time delay. The drive mechanism would then fire the staples from the staple cartridge 172 into the compressed tissues and thus ensure a uniform staple formation. The surgical stapler 100 thus provides a time delay prior to stapling to ensure tissue compression.

Although shown as an endoscopic surgical stapler, the present drive system may be used with any surgical stapling device known in the art, such as endoscopic surgical stapling devices, a multi-fire GIA surgical stapler, a TA surgical stapling device, and/or any other surgical stapler device known in the art. The present instrument may also be used with a single drive surgical stapler that drives both the clamping device of the jaws 21, 22 and the stapling device.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure.

Other elements, steps, methods and techniques that are insubstantially different from those described above and/or in the appended claims are also intended to be within the scope of the disclosure.

What is claimed is:

1. A powered endoscopic surgical apparatus, comprising:
    a handle including a housing and a power source supported in the housing;
    an endoscopic portion extending distally from the housing of the handle;
    an end effector assembly coupled to a distal end portion of the endoscopic portion, the end effector assembly including a pair of jaws configured to perform a surgical function, at least one of the jaws being movable with respect to the other jaw;
    a driving member extending between the handle and the end effector assembly, the driving member configured to translate along a drive path thereof to selectively actuate the end effector assembly;
    a motor powered by the power source and connected to the driving member such that the driving member is translated along the drive path upon actuation of the motor;
    a sensor disposed along the drive path of the driving member;
    a graphical display supported in the housing and operatively coupled to the sensor, the graphical display configured to receive a first signal from the sensor corresponding to a location of the driving member along the drive path and display a visual indication corresponding to the location of the driving member along the drive path; and
    a controller operatively coupled to the sensor and the motor, the controller configured to modulate the motor upon receiving a second signal from the sensor corresponding to the location of the driving member along the drive path.

2. The powered endoscopic surgical apparatus according to claim 1, wherein the sensor includes a resistor strip coupled to a travel surface of the drive path, wherein the first signal is a change in resistance detected by the resistor strip as the driving member translates along the travel surface of the drive path.

3. The powered endoscopic surgical apparatus according to claim 2, wherein the graphical display includes a series of discreet segments, each discreet segment of the series of discreet segments configured to illuminate in succession to indicate a travel distance of the driving member along the drive path until the end effector assembly is actuated.

4. The powered endoscopic surgical apparatus according to claim 3, wherein the controller is operatively coupled to the graphical display such that upon actuation of the end effector assembly, the graphical display is configured to receive a third signal from the controller and transmit the visual indication that the end effector assembly has been fired.

5. The powered endoscopic surgical apparatus according to claim 2, wherein the change in resistance detected by the resistor strip corresponds to a change in the location of the driving member along the travel surface of the drive path.

6. The powered endoscopic surgical apparatus according to claim 1, wherein the sensor is a non-contact sensor located along the drive path, the non-contact sensor operatively coupled to a portion of the driving member to determine a distance between the non-contact sensor and the portion of the driving member.

7. The powered endoscopic surgical apparatus according to claim 6, wherein in an initial orientation of the driving member, the non-contact sensor is disposed adjacent the portion of the driving member and spaced apart a first distance from the portion of the driving member.

8. The powered endoscopic surgical apparatus according to claim 7, wherein upon translation of the driving member along the drive path, the non-contact sensor is spaced apart from the portion of the driving member a second distance greater than the first distance of the initial orientation of the driving member and the non-contact sensor transmits the second signal to the controller to modulate the motor.

9. The powered endoscopic surgical apparatus according to claim 8, wherein the non-contact sensor includes a hall effect sensor and the portion of the driving member includes a magnetic member, the hall effect sensor configured to determine a change in a magnetic field of the magnetic member from the first distance between the hall effect sensor and the magnetic member to the second distance between the hall effect sensor and the magnetic member.

10. The powered endoscopic surgical apparatus according to claim 9, wherein the magnetic member is disposed on a distal portion of the driving member.

11. The powered endoscopic surgical apparatus according to claim 1, wherein the handle further includes:

a closing lever supported on the housing; and
a closure member having a proximal end portion operatively connected to the closing lever and a distal end portion extending through the endoscopic portion to the end effector assembly, wherein manual actuation of the closing lever imparts linear movement of the closure member such that the distal end portion of the closure member engages and actuates the end effector assembly to open and close the pair of jaws.

12. The powered endoscopic surgical apparatus according to claim 11, wherein the closing lever includes an electrical contact configured to send a fourth signal to the graphical display upon manual actuation of the closing lever.

13. The powered endoscopic surgical apparatus according to claim 1, wherein the power source is a battery.

14. The powered endoscopic surgical apparatus according to claim 1, wherein the end effector assembly is a stapling mechanism.

15. The powered endoscopic surgical apparatus according to claim 14, wherein translation of the driving member actuates the end effector assembly to perform a stapling function.

* * * * *